US012758735B2

(12) United States Patent
Babbage et al.

(10) Patent No.: US 12,758,735 B2
(45) Date of Patent: Oct. 13, 2026

(54) RESPIRATORY THERAPY SYSTEM AND APPARATUS

(71) Applicant: Fisher & Paykel Healthcare Limited, Auckland (NZ)

(72) Inventors: Sean Joel Babbage, Auckland (NZ); Simei Gomes Wysoski, Auckland (NZ); Sarah Emily Lowe, Auckland (NZ); Andrew Paul Maxwell Salmon, Auckland (NZ); Christopher Harding Campbell, Auckland (NZ); Hamish Chan, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1054 days.

(21) Appl. No.: 17/753,586

(22) PCT Filed: Sep. 9, 2020

(86) PCT No.: PCT/NZ2020/050100

§ 371 (c)(1),
(2) Date: Mar. 8, 2022

(87) PCT Pub. No.: WO2021/049953

PCT Pub. Date: Mar. 18, 2021

(65) Prior Publication Data

US 2022/0347423 A1 Nov. 3, 2022

Related U.S. Application Data

(60) Provisional application No. 62/897,996, filed on Sep. 9, 2019.

(51) Int. Cl.
*A61M 16/00* (2006.01)
*A61M 16/16* (2006.01)

(52) U.S. Cl.
CPC ........ *A61M 16/16* (2013.01); *A61M 16/0066* (2013.01); *A61M 16/0003* (2014.02)

(58) Field of Classification Search
CPC .............. A61M 16/16; A61M 16/0066; A61M 16/0003; A61M 16/0069; A61M 16/109;
(Continued)

(56) References Cited

U.S. PATENT DOCUMENTS 3,724,454 A 4/1973 Brown
3,806,102 A 4/1974 Valenta et al.
(Continued)

FOREIGN PATENT DOCUMENTS

EP 0 777 507 B1 6/1997
EP 1287843 A2 3/2003
(Continued)

OTHER PUBLICATIONS

Search Report in corresponding International Patent Application No. PCT/NZ2020/050100, mailed Nov. 9, 2020, in 5 pages.
(Continued)

*Primary Examiner* — Brandy S Lee
*Assistant Examiner* — Tina Zhang
(74) *Attorney, Agent, or Firm* — Knobbe, Martens, Olson & Bear, LLP

(57) ABSTRACT

Described is a respiratory therapy system that comprises a respiratory therapy apparatus that is configured to provide a flow of breathable gas at, at least a first pressure and a second pressure to a patient. The respiratory therapy apparatus comprises a flow generator configured to provide the flow of breathable gas, a controller, coupled to a trigger sensor, to control respiratory therapy apparatus operations, a breathing conduit assembly that conveys the breathable gas to a patient via a patient interface, a trigger that produces a signal detectable by the trigger sensor. The controller is
(Continued)

configured to control the flow generator to provide the flow of breathable gas at, at least the first pressure or the second pressure based on detection of the signal from the trigger.

13 Claims, 16 Drawing Sheets

(58) Field of Classification Search
CPC ............ A61M 16/1095; A61M 16/125; A61M 16/161; A61M 16/202; A61M 2016/0018; A61M 2016/0027; A61M 2202/0208; A61M 2202/0225; A61M 2205/13; A61M 2205/15; A61M 2205/3306; A61M 2205/3334; A61M 2205/3344; A61M 2205/3358; A61M 2205/3368; A61M 2205/3569; A61M 2205/3584; A61M 2205/3592; A61M 2205/3653; A61M 2205/505; A61M 2205/581; A61M 2205/582; A61M 2205/583; A61M 2230/06; A61M 2230/205; A61M 2240/00; A61M 16/024; A61M 16/0858; A61M 16/0833; A61M 16/0051; A61M 16/06; A61M 16/0666; A61M 16/0816; A61M 16/0875; A61M 16/0883; A61M 2202/0488; A61M 16/0683; A61M 2205/07; A61M 2205/18; A61M 2205/3331; A61M 2205/35; A61M 16/00; A61M 16/12; A61M 2016/003; A61M 2205/502; A61M 2016/0015; A61M 16/201–209; A61B 5/0205; A61B 5/024
See application file for complete search history.

(56) References Cited

U.S. PATENT DOCUMENTS 3,807,445 A * 4/1974 McPhee .................. F16K 37/00 137/557
4,192,836 A 3/1980 Bartscher et al.
4,459,983 A 7/1984 Beyreuther et al.
5,743,879 A * 4/1998 Kriesel ................ A61M 5/152 604/157
5,839,436 A * 11/1998 Fangrow, Jr. ....... A61M 16/208 128/205.24
5,943,473 A 8/1999 Levine
6,805,120 B1 10/2004 Jeffrey et al.
7,044,129 B1 5/2006 Truschel et al.
7,305,987 B2 12/2007 Scholller et al.
D582,427 S 12/2008 Neuhaus
D657,368 S 4/2012 Magee et al.
D667,838 S 9/2012 Magee et al.
8,439,031 B1 5/2013 Rothermel et al.
D739,427 S 9/2015 Jung et al.
D761,863 S 7/2016 Debitsch et al.
D772,252 S 11/2016 Myers et al.
9,737,675 B2 8/2017 Frame et al.
D806,717 S 1/2018 Bae et al.
10,016,169 B2 7/2018 Meador et al.
D831,059 S 10/2018 Bao
D835,657 S 12/2018 Anzures et al.
D835,666 S 12/2018 Saleh et al.
D835,667 S 12/2018 Saleh et al.
10,226,200 B2 3/2019 Vassallo et al.
D846,583 S 4/2019 Martin et al.
10,314,990 B2 6/2019 Richards-Kortum et al.
10,342,950 B2 7/2019 Bath et al.
10,369,309 B2 8/2019 Feldhahn et al.
D885,410 S 5/2020 Butler
D887,441 S 6/2020 Lorca Norambuena
D892,141 S 8/2020 Clifford et al.
D892,142 S 8/2020 Clifford et al.
D892,832 S 8/2020 Onuma
D892,833 S 8/2020 Onuma
D893,547 S 8/2020 Dumas et al.
10,864,343 B2 12/2020 Bath et al.
10,905,843 B2 2/2021 Smith
D913,304 S 3/2021 VanDuyn et al.
D914,039 S 3/2021 Zimmerman et al.
D914,726 S 3/2021 Gouliard et al.
D916,721 S 4/2021 Kirkeby
D916,743 S 4/2021 Sim et al.
D916,878 S 4/2021 Kim et al.
D918,224 S 5/2021 Velamuri et al.
D922,405 S 6/2021 Norman
11,039,797 B2 6/2021 Meador et al.
D928,190 S 8/2021 Hartman et al.
D928,813 S 8/2021 Nurutdinov et al.
11,135,388 B2 10/2021 Ronayne
D940,729 S 1/2022 Campbell et al.
D941,849 S 1/2022 Knowles et al.
D978,157 S 2/2023 Han et al.
12,048,810 B2 7/2024 Dennis et al.
D1,092,528 S 9/2025 Campbell et al.
2003/0029451 A1 2/2003 Blair et al.
2003/0047185 A1 3/2003 Olsen et al.
2004/0040559 A1* 3/2004 Moody ............. A61M 16/0463 128/204.24
2004/0244804 A1 12/2004 Olsen et al.
2005/0150494 A1 7/2005 Devries et al.
2006/0048782 A1* 3/2006 Gossweiler ............ A62B 23/02 128/205.12
2006/0174882 A1 8/2006 Jagger et al.
2009/0194108 A1 8/2009 Newman, Jr.
2009/0301482 A1* 12/2009 Burton .............. A61M 16/0816 417/44.1
2010/0051029 A1* 3/2010 Jafari ................ A61M 16/0051 128/204.23
2010/0078024 A1 4/2010 Andrieux et al.
2010/0228224 A1* 9/2010 Pyles .................... A61M 5/142 177/1
2011/0308518 A1 12/2011 Mcgroary et al.
2012/0220817 A1 8/2012 Castillon et al.
2012/0260718 A1 10/2012 Sparks et al.
2012/0272964 A1* 11/2012 Loser .................. A61M 16/161 128/204.23
2013/0228180 A1 9/2013 Ahmad et al.
2013/0267793 A1 10/2013 Meador et al.
2014/0000606 A1 1/2014 Doyle et al.
2014/0014110 A1 1/2014 Adams
2014/0166013 A1 6/2014 Stenzler et al.
2014/0277914 A1 9/2014 Fish et al.
2015/0059764 A1* 3/2015 Metelits .............. A61M 16/202 128/207.18
2015/0075524 A1 3/2015 Millar et al.
2015/0083123 A1 3/2015 Tero
2015/0186023 A1 7/2015 Alisanski et al.
2015/0258291 A1 9/2015 Richards-Kortum et al.
2016/0256642 A1 9/2016 Soysa et al.
2017/0224234 A1 8/2017 Ahlmen et al.
2017/0304570 A1 10/2017 Landis et al.
2018/0015245 A1 1/2018 Frame et al.
2018/0071469 A1 3/2018 Oldfield et al.
2018/0110948 A1 4/2018 Dellaca et al.
2018/0140927 A1 5/2018 Kito et al.
2018/0236196 A1* 8/2018 Palm ..................... A61M 16/20
2019/0083001 A1 3/2019 Stamatopoulos et al.
2019/0160241 A1* 5/2019 Boulanger ............ A61M 16/00
2019/0167937 A1 6/2019 Sims
2019/0184128 A1 6/2019 Lucio
2020/0246548 A1* 8/2020 Bill ..................... A61M 5/3155
2021/0023318 A1 1/2021 Tatum
2021/0038088 A1 2/2021 Atallah et al.
2021/0181932 A1 6/2021 Han et al.
2021/0228832 A1 7/2021 Parrish et al.
2021/0299396 A1 9/2021 Mohan et al.
2022/0168536 A1 6/2022 Hsu et al.

(56) References Cited

U.S. PATENT DOCUMENTS

| | | | |
|---|---|---|---|
| 2024/0024602 A1 | 1/2024 | Peiris et al. |
| 2025/0381358 A1 | 12/2025 | Hsu et al. |

FOREIGN PATENT DOCUMENTS

| | | | |
|---|---|---|---|
| EP | 2 123 321 | A1 | 11/2009 |
| EP | 1 061 981 | B1 | 9/2010 |
| EP | 2644220 | A1 | 10/2013 |
| JP | 52-105996 | | 8/1977 |
| WO | WO 2005/063323 | A1 | 7/2005 |
| WO | WO 09/145646 | | 12/2009 |
| WO | WO 2010/033429 | A1 | 3/2010 |
| WO | WO 2013/067580 | A1 | 5/2013 |
| WO | WO 2013/154439 | | 10/2013 |
| WO | WO 2014/085431 | | 6/2014 |
| WO | WO 2015/165845 | | 11/2015 |
| WO | WO 2016/133406 | | 8/2016 |
| WO | 2017/096428 | A1 | 6/2017 |
| WO | WO 2017/126980 | | 7/2017 |
| WO | WO 2018/033863 | | 2/2018 |
| WO | WO 2018/042355 | | 3/2018 |
| WO | WO 2019/193535 | | 10/2019 |
| WO | WO 2019/245391 | | 12/2019 |
| WO | WO 20/122739 | | 6/2020 |
| WO | WO 2020/188526 | | 9/2020 |
| WO | WO 2021/046537 | A1 | 3/2021 |
| WO | WO 2021/049953 | A1 | 3/2021 |
| WO | WO 2022/058982 | | 3/2022 |

OTHER PUBLICATIONS

Written Opinion in corresponding International Patent Application No. PCT/NZ2020/050100, mailed Nov. 9, 2020, in 10 pages.

Bernstein, Bill. DreamStation CPAP UI, Dec. 19, 2015, Bill Bernstein—UI, UX, Jan. 16, 2024, Accessed on the internet: https://bernstein.work/dreamstation-cpap (Year: 2015).

Worthington, Michael. Warm Touch GUI Redesign, Nov. 2, 2018, Michael Worthington Designs, Jan. 16, 2024, Accessed on the internet: https://www.michaelworthingtondesigns.com/ui-work/ (Year: 2018).

* cited by examiner

RESPIRATORY THERAPY SYSTEM AND APPARATUS

FIELD OF THE INVENTION

The present invention relates to a respiratory therapy system and apparatus.

BACKGROUND TO THE INVENTION

Positive End Expiratory Pressure (PEEP) and/or Peak Inspiratory Pressure (PIP) can be controllably provided to a patient during respiration, resuscitation or assisted respiration (ventilation). PEEP is the pressure above atmospheric pressure in the airway throughout the expiratory phase of positive pressure ventilation. PIP is the desired highest pressure applied to the lungs during inspiration. The patients may be neonates or infants who require breathing assistance or resuscitation. In applying PEEP, the patient's upper airway and lungs are held open by the applied pressure.

An example of such respiratory therapy apparatus is provided in PCT publication WO 03/066146A1 which discloses a connector for use in a respiratory therapy apparatus for resuscitating an infant or neonate. The connector includes a pressure regulator having a manifold with an inlet and two outlets. A first outlet supplies the respiratory gases to the infant. A second outlet can be used to vary pressure between a specified PIP and PEEP through a user (i.e. healthcare professional) manually occluding the orifice, such as through the use of their finger. Also described in the use of a valve that sits between the inlet and the orifice, and opens at a predetermined flow rate, that assists to maintain the pressure in the manifold at a constant level.

Another example is provided by PCT publication WO 2012/030232 that discloses a device similar to that of WO 03/066146A1 that includes a breath indicator that signals when the patient is inhaling and exhaling. Again, a healthcare professional manually occludes the orifice to vary pressure between the PIP and PEEP and observes the breath indicator so that they can monitor the infant's breathing.

Another example is given by PCT publication WO 2014/003578 that discloses a device similar to that of WO 03/066146A1. Again, the pressure regulator may be used to vary the pressure between PIP and PEEP by selective occlusion of the orifice, such as by placement of a finger over it. Moreover, the pressure at which the valve operates may be adjusted by adjusting the relative position of the valve seat.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY OF THE INVENTION

In a first aspect the disclosure relates to the delivery of ventilation to a patient through the use of a respiratory therapy system, configured to supply breathable gases to the patient at a pressure elevated above atmospheric pressure, and wherein the respiratory therapy system is configured to supply gas at, at least a first and a second pressure, based on the use of a trigger that selects between the gas pressure to be delivered.

In a further aspect the disclosure relates to a respiratory therapy system, the respiratory therapy system comprising:

a respiratory therapy apparatus, configured to provide at least a first pressure and a second pressure to a patient, the respiratory therapy apparatus comprising

- a flow generator configured to supply a breathable gas to a patient,
- a trigger sensor,
- a controller, coupled to the trigger sensor, to control respiratory therapy apparatus operations;

a breathing conduit that conveys the breathable gas to a patient via a patient interface;

a trigger that produces a signal detectable by the trigger sensor; and wherein the controller is configured to adjust the flow generator to deliver at least the first pressure or the second pressure based on use of the trigger.

In a further aspect the disclosure relates to a respiratory therapy system, the respiratory therapy system comprising:

a respiratory therapy apparatus, configured to provide a flow of breathable gas at, at least a first pressure and a second pressure to a patient, the respiratory therapy apparatus comprising

- a flow generator configured to provide the flow of breathable gas,
- a controller, coupled to a trigger sensor, to control respiratory therapy apparatus operations;

a breathing conduit that conveys the breathable gas to a patient via a patient interface;

a trigger that produces a signal detectable by the trigger sensor; and wherein the controller is configured to adjust the flow generator to provide the flow of breathable gas at, at least the first pressure or the second pressure based on detection of the signal from trigger.

Preferably the first pressure is positive end expiratory pressure. Preferably the second pressure is peak inspiratory pressure.

In a further aspect the disclosure relates to a respiratory therapy system, the respiratory therapy system comprising:

- a respiratory therapy apparatus, configured to provide at least positive end expiratory pressure (PEEP) and peak inspiratory pressure (PIP), the respiratory therapy apparatus comprising
  - a flow generator configured to supply a breathable gas to a patient,
  - a trigger sensor,
  - a controller, coupled to the trigger sensor, to control respiratory therapy apparatus operations;
- a breathing conduit that conveys the breathable gas to a patient via a patient interface;
- a trigger that produces a signal detectable by the trigger sensor; and
- wherein the controller is configured to adjust the flow generator to deliver at least PEEP or PIP based on use of the trigger.

In a further aspect the disclosure relates to a respiratory therapy apparatus, configured to provide a flow of breathable gas at, at least a first pressure and a second pressure to a patient, the respiratory therapy apparatus comprising;

- a flow generator configured to provide the flow of breathable gas,
- a controller, coupled to a trigger sensor, to control respiratory therapy apparatus operations;

the respiratory therapy apparatus being configured to operate with a breathing conduit assembly that conveys the breathable gas to a patient via a patient interface, and a trigger that produces a signal detectable by the trigger sensor; and wherein the controller is configured to control the flow generator to provide the flow of breathable gas at, at least the first pressure or the second pressure based on detection of the signal from the trigger.

In a further aspect the disclosure relates to a connector element for use with a respiratory therapy system which conveys gases to a patient requiring resuscitation and/or breathing assistance, the connector element comprising a housing comprising an inlet adapted to be in fluid communication or integrated with a respiratory therapy apparatus that provides a supply of breathable gases, an outlet adapted to be in fluid communication with a patient interface, a trigger that produces a signal detectable by a trigger sensor on, or in, the respiratory therapy apparatus, wherein the respiratory therapy apparatus comprises a controller configured to adjust gas pressure provided to the inlet based on use of the trigger.

In a further aspect the disclosure relates to a method of providing respiratory therapy to a patient comprising conveying a breathable gas to a patient via a respiratory therapy apparatus comprising a flow generator and a trigger, detecting a signal produced by the trigger, and providing a positive end expiratory pressure (PEEP) or a peak inspiratory pressure (PIP) to the patient in response to the detected signal.

In a further aspect the disclosure relates to a method of providing respiratory therapy to a patient, comprising providing a respiratory therapy apparatus, configured to provide at least positive end expiratory pressure (PEEP) and peak inspiratory pressure (PIP), the respiratory therapy apparatus comprising a flow generator configured to supply a breathable gas to a patient, at least one trigger sensor, and a controller, coupled to the trigger sensor, to control respiratory therapy apparatus operations, and a breathing conduit that conveys the breathable gas to a patient via a patient interface, providing a trigger that produces a signal detectable by the trigger sensor; and operating the respiratory therapy apparatus to deliver at least positive end expiratory pressure and peak inspiratory pressure, wherein the controller is configured to adjust the flow generator to deliver at least PEEP or PIP based on use of the trigger mechanism.

Any one or more of the following embodiments may relate to any of the aspects described herein or any combination thereof.

Preferably the second pressure is greater than the first pressure.

Preferably the connector element comprises a hollow cylindrical body.

In some embodiments the connector element comprises a monitoring port.

In some embodiments the monitoring port is shaped to receive a valve.

Preferably the trigger is a biased trigger.

In one embodiment the trigger is biased towards a non-active position such that the controller is configured to deliver positive end expiratory pressure (PEEP).

In an alternate embodiment the trigger is biased towards a non-active position such that the controller is configured to deliver peak inspiratory pressure (PIP).

In one embodiment the production of a signal, detectable from the trigger sensor, correlates to the controller controlling the respiratory therapy apparatus to deliver positive end expiratory pressure (PEEP).

In an alternate embodiment the production of a signal, detectable from the trigger sensor, correlates to the controller controlling the respiratory therapy apparatus to deliver peak inspiratory pressure (PIP).

In one embodiment the respiratory therapy apparatus delivers positive end expiratory pressure (PEEP) for the duration that the trigger is activated.

In alternate embodiment the respiratory therapy apparatus delivers peak inspiratory pressure (PIP) for the duration that the trigger is activated.

Preferably the controller regulates the gas pressure delivered by the respiratory therapy apparatus via the use of a control loop mechanism. More preferably said control loop mechanism employs feedback that includes at least a pressure sensor in the gas flow path.

In one embodiment the respiratory therapy apparatus comprises a connector, disposed between the breathing conduit and the patient interface. In this embodiment the trigger mechanism may be disposed on the connector.

In one embodiment the respiratory therapy apparatus comprises a humidifier configured to humidify the breathable gas.

In one embodiment the humidifier is integrated with the respiratory therapy apparatus.

In one embodiment the breathing conduit assembly comprises a heated conduit. More preferably the heated conduit comprises a heater wire. Preferably the heater wire is connected to the controller.

In one embodiment the trigger is connected to the trigger sensor via a sensor line. More preferably the sensor line is selected from a pneumatic or electrical line.

In one embodiment the triggers produces a signal that is detected by a trigger sensor wherein the signal is an electrical signal.

In one embodiment the signal is indicative of the trigger being actuated.

In one embodiment the trigger is a switch that, upon activation, completes a circuit which is then detected by the trigger sensor or the controller.

In one embodiment the trigger sensor may detect an electrical signal that is generated when the trigger is actuated.

In one embodiment actuation of the trigger generates an electrical signal that is detected by the trigger sensor that causes the controller to adjust the target gas pressure.

In one embodiment actuation of the trigger may generate an electrical signal that is detected by the trigger sensor that causes the controller to adjust the target gas pressure provided to the inlet of the connector element to a first pressure level for the duration that the trigger is actuated.

In one embodiment the electrical switch may have two or more positions, wherein an electrical signal is delivered when the switch is in one of the positions.

In one embodiment the trigger may comprise two or more electrical switches, wherein an electrical signal is generated when a user actuates the first switch, the electrical signal generation only ceasing when the user actuates a second or subsequent switch.

In one embodiment the sensor line is located externally of the breathing conduit.

Preferably the sensor line is located internally of the connector element.

Preferably the trigger sensor is a pressure sensor.

In one embodiment the trigger sensor is located on, or in, the breathing conduit proximate to the patient interface.

In an alternate embodiment the trigger sensor is located on, or in, the patient interface.

In an alternate embodiment the trigger sensor is located on the respiratory therapy apparatus.

In one embodiment the trigger is a compressible chamber.

Preferably compression of the compressible chamber is detected by the trigger sensor. Preferably the trigger sensor is a differential pressure sensor.

Preferably the compressible chamber is formed by the trigger and the trigger sensor line.

Preferably the trigger sensor is configured to provide an output to the controller indicative of a compressible chamber pressure.

Preferably the trigger sensor is a gauge, absolute or differential pressure sensor.

Preferably the controller is configured to control the respiratory therapy system to deliver the first pressure when the compressible chamber pressure is below a compressible chamber pressure threshold, and the second pressure when the compressible chamber pressure is above the compressible chamber pressure threshold.

Preferably the controller is configured to control the respiratory therapy system to deliver the second pressure when the compressible chamber pressure is below a compressible chamber pressure threshold, and the first pressure when the compressible chamber pressure is above the compressible chamber pressure threshold.

In one embodiment the respiratory therapy apparatus comprises a connector element, the connector element having a first outlet in fluid communication with the patient interface, an inlet in fluid communication with the breathing conduit, and an aperture that defines a chamber, and wherein the trigger is located on the chamber.

In one embodiment a portion of the trigger sensor line terminates inside the connector element at the trigger.

In one embodiment the connector element is "T"-shaped and comprises a hollow cylindrical body with a gases inlet, a gases outlet, a monitoring port, and a trigger port.

In one embodiment the connector element comprises a monitoring port.

Preferably the respiratory therapy apparatus comprises a vent arrangement.

Preferably the vent arrangement is located in the connector element or in the breathing conduit assembly.

Preferably the controller controls both the operation of both the respiratory therapy apparatus and the humidifier.

Preferably the respiratory therapy apparatus is adapted to provide gas selected from a) pure oxygen, or b) ambient air, or c) a combination of pure oxygen and ambient air.

In one embodiment the oxygen provided to the respiratory therapy apparatus is provided by a low- or a high-pressure source.

Preferably the controller is configured to detect fitment of the patient interface on the patient.

Preferably the controller activates the respiratory therapy apparatus to provide positive end expiratory pressure upon detection of mask fitment on a patient. In one embodiment the controller detects flow conductance as an indicator of mask fitment on a patient.

Preferably the respiratory therapy apparatus provides a first pressure level of gas to a patient upon detection of mask fitment on a patient. Preferably the first pressure level is approximately equal to positive end expiratory pressure.

Preferably the trigger sensor detects the first pressure level of gas. In one embodiment the trigger sensor is located within the respiratory therapy apparatus. In an alternate embodiment the trigger sensor is located in the breathing conduit or the patient interface.

Preferably the respiratory therapy apparatus provides a second pressure level of gas to a patient upon detection of a trigger by the trigger sensor. Preferably the second pressure level is approximately equal to positive end expiratory pressure.

Preferably the respiratory therapy apparatus is configured to detect a leak in the patient interface.

In one embodiment the trigger is a pneumatic trigger comprising a moveable member.

In one embodiment the trigger is a pneumatic trigger comprising a housing and moveable member, wherein the housing and moveable member combine to define a compressible chamber.

In one embodiment the trigger comprises a plurality of projections within the chamber to define a boundary for the inward deflection of the moveable member.

In one embodiment the trigger comprises projections that provide haptic feedback to the user regarding the location of their thumb/finger with respect to the moveable member.

In one embodiment the sensor line connects to the chamber through an opening.

Preferably the trigger includes an ambient reference opening which inhibits the ability of false triggers.

Preferably the breathing conduit assembly comprises one or more retention mechanisms to retain the trigger sensor line. In one embodiment the retention mechanism is disposed within the internal diameter of a breathing conduit of the breathing conduit assembly. In an alternate embodiment the retention mechanism located on the exterior surface of the breathing conduit of the breathing conduit assembly.

Preferably the respiratory therapy apparatus is for resuscitation of a neonate.

Preferably the calcium-source reverting agent is about 2.5, 3.0, 3.5, 4.0, 4.5, 5.0, 5.5, 6.0, 6.5, 7.0, 7.5, 8.0, 8.5, 9.0 or 9.5% by weight of the superphosphate-reverting agent mixture, and suitable ranges may be selected from between any of these values. More preferably the magnesium-source reverting agent is about 4.0, 4.5, 5.0, 5.5, 6.0, 6.5, 7.0, 7.5, 8.0, 8.5 or 9% by weight of the superphosphate-reverting agent mixture, and suitable ranges may be selected from between any of these values.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

As used herein, the phrases "respiratory therapy system" and "breathing assistance system" are used interchangeably.

BRIEF DESCRIPTION OF THE DRAWINGS

The disclosure will now be described by way of example only and with reference to the drawings in which.

DETAILED DESCRIPTION OF THE INVENTION

Figure 1A:
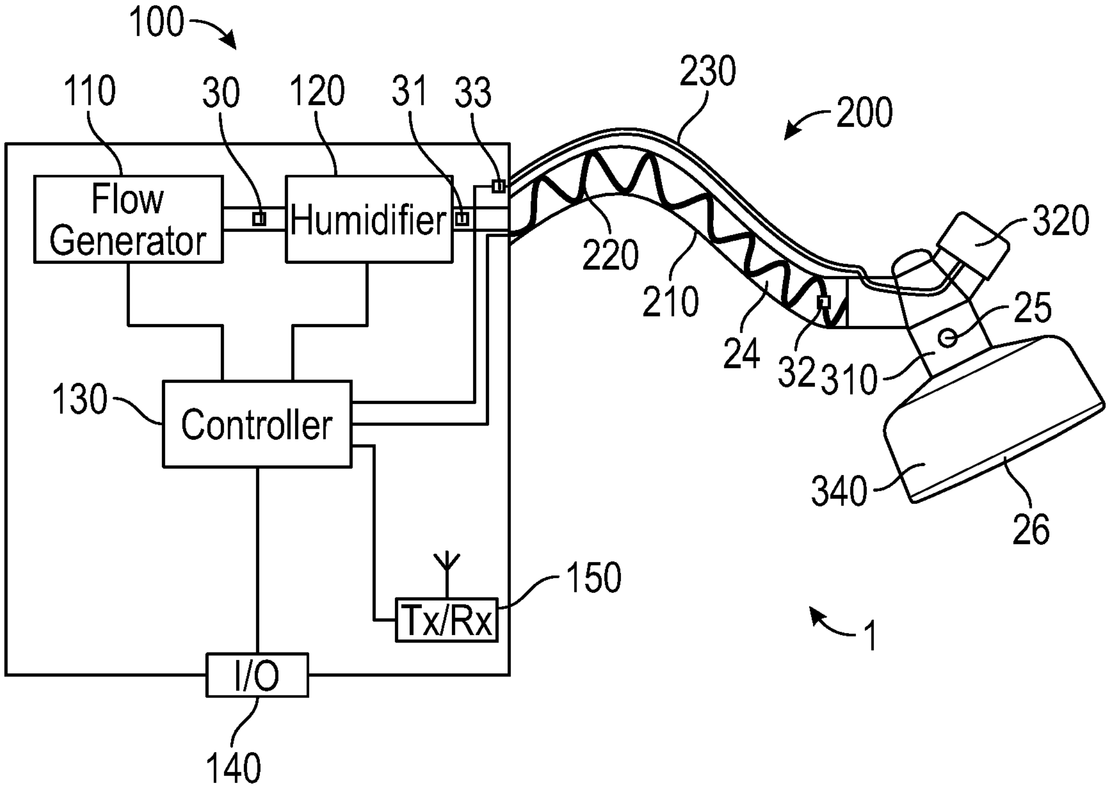
FIG. 1A shows a respiratory therapy system in diagrammatic form.

The present disclosure relates to a respiratory therapy system.

Described is the use of a respiratory therapy system 1, having a respiratory therapy apparatus 100, breathing conduit assembly 200, trigger assembly 320 and patient interface 340.

A respiratory therapy apparatus 100 comprising a flow generator 110 to generate a pressurised flow of gas, has several advantages over using a typical wall source. For example, it allows the provided pressure to be varied. It also provides the ability to detect and/or mitigate leak at the patient interface 340, and also means fewer devices are needed to provide a range of care or a range of respiratory therapies. Additionally, a respiratory therapy apparatus 100 having an integrated humidifier 120, can be controlled by a single controller 130, which allows for monitoring and control of various flow and/or pressure parameters. The respiratory therapy system 1 may be able to provide other forms of therapy thereby expanding the care continuum for the device and making for an easier transition between different types of respiratory support as the patient's condition changes. Combining devices further provides the benefit of reducing the capital expenditure of healthcare providers.

1. OVERVIEW

A respiratory therapy system 1 is shown in FIG. 1. In general terms, the respiratory therapy system 1 comprises a respiratory therapy apparatus 100 (which can include a flow generator 110, a trigger sensor 33, and a controller 130), a breathing conduit assembly 200, a trigger 320, and a patient interface 340. In at least one configuration, the flow generator 110 can be in the form of a blower 110.

Figure 1B:
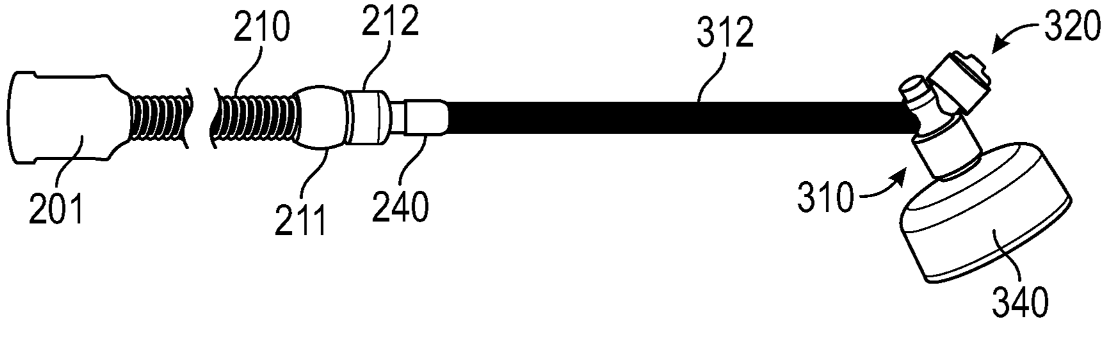
FIG. 1B shows a breathing conduit assembly, connector element and patient interface.

As shown in FIG. 1B, the respiratory therapy system 1 may also include a connector element 310. When present, the connector element 310 connects the patient interface 340 to the breathing conduit assembly 200. The breathing conduit assembly 200 may comprise a breathing conduit 210. The breathing conduit 210 may comprise a hose and one or more hose end connectors. The breathing conduit 210 may be an assembly of the hose and one or more hose end connectors. The one or more hose end connectors may be disposed at respective ends of the hose. The hose end connectors may allow the breathing conduit 210 to pneumatically and/or electrically connect to other components (e.g. the patient interface 340, respiratory therapy apparatus 100, connector element 310 etc.). The breathing conduit 210 may include a first hose end connector at a first end of the hose, and a second hose end connector at a second end of the hose. The breathing conduit assembly 200 may comprise an interface conduit 312. The illustrated breathing conduit assembly 200 comprises the interface conduit 312 and the breathing conduit 210. The breathing conduit assembly 200 may also include a patient end connector 212. The patient end connector 212 can interface or connect the interface conduit 312 with the breathing conduit 210. In other words, the patient end connector 212 can facilitate connection of the interface conduit 312 to the breathing conduit 210.

The trigger 320 may connect to a trigger sensor line 230 configured to provide a signal to the controller 130.

The respiratory therapy apparatus 100 may also include a humidifier 120 in fluid connection with the flow generator 110.

Also included is a controller 130, and a user interface 140 (comprising, for example, a display and input device(s) such as button(s), a touch screen, or the like). The controller 130 is configured or programmed to control the components of the respiratory therapy system 1. The controller 130 is configured or programmed to control and/or interact with components of the respiratory therapy apparatus 100, including: operating the flow generator 110 to create a flow of gas (gas flow) for delivery to a patient, operating the humidifier 120 (if present) to humidify and/or heat the generated gas flow, receive one or more inputs from sensors and/or the user interface 140 for reconfiguration and/or user-defined operation of the respiratory therapy apparatus 100, and output information (for example on the display) to the user. An example of a respiratory therapy apparatus 100 with an integrated humidifier is described in WO 2016/207838A1, which is incorporated by reference. The gas flow provided to the patient may be provided at a target flow rate. Alternatively, the gas flow provided to the patient may be provided at a target pressure. The user could be a patient (i.e. receiving the respiratory therapy), healthcare professional, or anyone else interested in using the respiratory therapy system 1.

Patient interfaces are used to provide respiratory therapy to the airways of a person suffering from any of a number of respiratory illnesses or conditions. Such therapies may include, but are not limited to, infant resuscitation, positive airway pressure (PAP) therapy, continuous positive airway pressure (CPAP) therapy, non-invasive ventilation (NIV), nasal high flow (NHF) therapy or other therapies.

In relation to infant resuscitation, when in utero, the lungs of a foetus are filled with fluid, and oxygen comes from the blood vessels of the placenta. At birth, the transition to continuous postnatal respiration occurs, assisted by the development of negative pressure in the lungs due to compression of the lungs by the birth canal. Also assisting the baby to breathe is the presence of surfactant that lines the alveoli to lower surface tension. The need for infant resuscitation can occur in a range of circumstances.

While most infants tolerate passage through the birth canal for the duration of the average contraction, the few that do not may require assistance to establish normal breathing at delivery. Resuscitation may also be needed by babies with intrapartum evidence of significant fetal compromise, babies being delivered before 35 weeks gestation (particularly since surfactant production does not begin until the 24th week of gestation and continues until the 34th week of gestation), babies being delivered vaginally by the breech, maternal infection and multiple pregnancies. Additionally, caesarean delivery is associated with an increased risk of problems with respiratory transition at birth requiring medical interventions, and especially for deliveries before 39 weeks gestation.

As stated above, the gas flow, which may be humidified, that is generated by the respiratory therapy apparatus 100 of the respiratory therapy system 1 is delivered to the patient via the breathing conduit assembly 200 through the patient terminal end 26 of the patient interface 340.

In at least one configuration, the patient interface 340 can be in the form of a sealed patient interface. In at least one configuration, the patient interface 340 can be in the form of a respiratory mask. The patient interface 340 can be configured to deliver a supply of positive air pressure to the patient's airway via a seal or cushion, of the patient terminal end 26, that forms an airtight seal in or around the patient's nose and/or mouth. The patient interface 340 can be a full-face, nasal, direct nasal and/or oral patient interface, which creates an airtight seal between the patient terminal end 26 and the nose and/or mouth of the patient. In at least one form, the seal or cushion can be held in place on the patient's face by headgear. In at least one form, the patient interface 340 can be held in place on the patient's face by the user or healthcare professional. Such sealed patient interfaces can be used to deliver pressure therapy to the patient. Alternative patient interfaces, for example those comprising nasal prongs can be used. In some examples, the nasal prongs may be sealing or non-sealing.

The breathing conduit 210 can have a heating element 220 to heat gas flow passing through the breathing conduit 210 to the patient. In one form, the heating element 220 can be a heater wire. The heating element 220 can be in the form of a length of conductive wire. The conductive wire may have a predetermined resistance. The heating element 220 can be under the control of a controller, whether the controller is a central controller (e.g. controller 130) or an auxiliary controller.

The breathing conduit assembly 200 and/or patient interface 340 can be considered part of respiratory therapy system 1. Alternatively, the breathing conduit assembly 200 and/or patient interface 340 can be considered peripheral to the respiratory therapy system 1. The respiratory therapy apparatus 100, breathing conduit assembly 200, and patient interface 340 can together form at least part of the respiratory therapy system 1. In other words, the respiratory therapy system 1 can comprise the respiratory therapy apparatus 100, breathing conduit assembly 200 and the patient interface 340. In one form, the respiratory therapy apparatus 100, breathing conduit assembly 200, and the patient interface 340 together form the respiratory therapy system 1. The trigger 320 and/or connector element 310 may be considered peripheral to the respiratory therapy system 1.

The controller 130 can control the respiratory therapy apparatus 100 to generate a gas flow at a desired pressure. The controller 130 can control the respiratory therapy apparatus 100 to generate a gas flow at a desired flow rate. In particular, the controller 130 can control the flow generator 110 to generate a gas flow at a desired pressure and/or flow rate.

In one embodiment the controller 130 controls one or more valves to control the mix of air and oxygen or other alternative gas.

The controller 130 controls the humidifier 120, if present, to humidify the gas flow and/or heat the gas flow to an appropriate level. The gas flow is directed out through the breathing conduit assembly 200 and patient interface 340 to the patient. The controller 130 can also control a humidifier heating element 220 of the humidifier 120 and/or the heating element 220 of the breathing conduit 210 to heat the gas to and/or maintain the gas at a desired temperature. The controller 130 can be programmed with or can determine a suitable target temperature and/or humidity of the gas flow. The controller 130 can be programmed with or can determine a suitable target temperature and/or humidity of the gas flow, and use one or more of the heating element 220, humidifier heating element 220 and the flow generator 110 to control flow and/or pressure to the target temperature and/or humidity. The target temperature and/or humidity of the heated gas can be set to achieve a desired level of therapy and/or comfort for the patient.

Operation sensors 30, 31 and 32, such as flow, temperature, humidity, and/or pressure sensors can be placed in various locations in the respiratory therapy apparatus 100 and/or the breathing conduit assembly 200 and/or patient interface 340. One or more outputs from the sensors 30, 31 and 32 can be monitored by the controller 130, to assist it to operate the respiratory therapy system 1 in a manner that provides optimal therapy. In some configurations, providing optimal therapy includes meeting a patient's inspiratory demand. In at least one configuration, providing optimal therapy includes providing a first target pressure to the patient at a first time, and a second target pressure to the patient at a second time. The second target pressure can be greater than the first target pressure. The second target pressure can be set to meet an inspiratory pressure target. The first target pressure can be set to meet an expiratory pressure target. The first target pressure can be greater than the second target pressure. The first target pressure can be set to meet an inspiratory pressure target. The second target pressure can be set to meet an expiratory pressure target.

The respiratory therapy apparatus 100 may have a transmitter 150, receiver 150, and/or transceiver 150 to enable the controller 130 to receive transmitted signals from the sensors and/or to control the various components of the respiratory therapy system 1. The controller 130 may receive transmitted signals from the sensors related to, or control components including but not limited to the flow generator 110, humidifier 120, humidifier heating element 220, or accessories or peripherals associated with the respiratory therapy apparatus 100 such as the breathing conduit assembly 200. For example, the transmitted signals can relate to, or are processed to instruct control of components. Additionally, or alternatively, the transmitter 150, receiver 150 and/or transceiver 150 may deliver data to a remote server or enable remote control of the respiratory therapy system 1.

The respiratory therapy system 1 is configured to provide respiratory therapy. The respiratory therapy may be a pressure therapy, such as a CPAP or bubble CPAP or nasal CPAP, delivered to a patient to assist with breathing and/or treat breathing disorders. The pressure therapy may involve the respiratory therapy system 1 providing pressure at, or near, the patient at one or more target pressures for one or more time windows. The pressure therapy can be infant resuscitation therapy, positive airway pressure therapy (PAP), continuous positive airway pressure therapy (CPAP), bi-level positive airway pressure therapy, non-invasive ventilation, bubble CPAP therapy or another form of pressure therapy. In some configurations, as illustrated, the device may provide bi-level positive airway pressure therapy to achieve infant resuscitation.

'Pressure therapy' as used in this disclosure may refer to delivery of pressure to a patient at a pressure of greater than or equal to about 4 $cmH_2O$. In some configurations, 'pressure therapy' may refer to the delivery of gases to a patient at a pressure of between about 20 $cmH_2O$ and about 30 $cmH_2O$, or between about 21 $cmH_2O$ and about 30 $cmH_2O$, or between about 22 $cmH_2O$ and about 30 $cmH_2O$, or between about 23 $cmH_2O$ and about 30 $cmH_2O$, or between about 24 $cmH_2O$ and about 30 $cmH_2O$, or between about 25 $cmH_2O$ and about 30 $cmH_2O$, or between about 20 $cmH_2O$ and about 25 $cmH_2O$, or between about 21 $cmH_2O$ and about 25 $cmH_2O$, or between about 22 $cmH_2O$ and about 25 $cmH_2O$.

In some configurations, the gas delivered to the patient is or comprises oxygen. In some configurations, the gas comprises a blend of oxygen or oxygen enriched gas, and ambient air. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%. In at least one configuration, the gases delivered may be of atmospheric composition. In at least one configuration, the gases delivered may be ambient air.

Figure 2A:
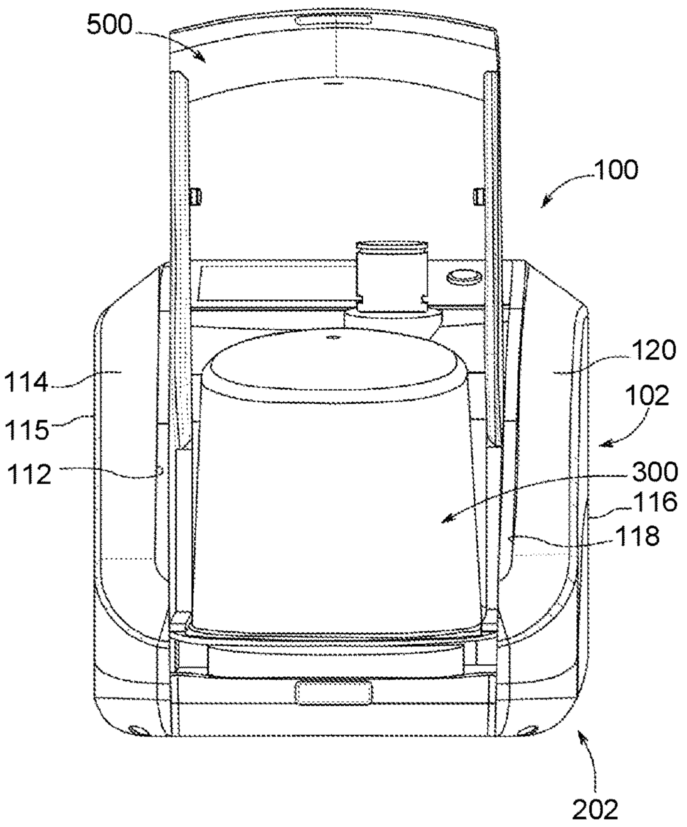
FIG. 2A is a front view of a respiratory therapy apparatus with a humidifier chamber in position and a raised handle/lever.
Figure 2B:
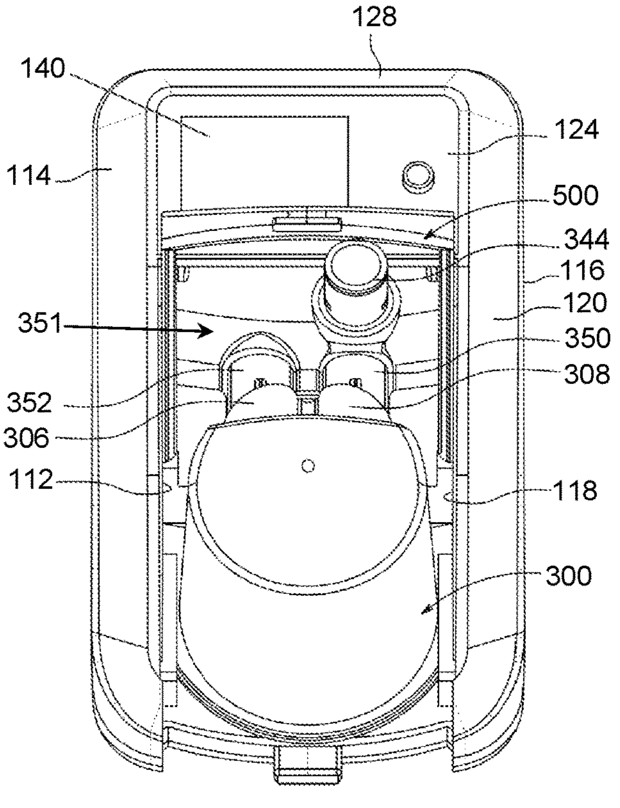
FIG. 2B is a top view corresponding to FIG. 2A.
Figure 2C:
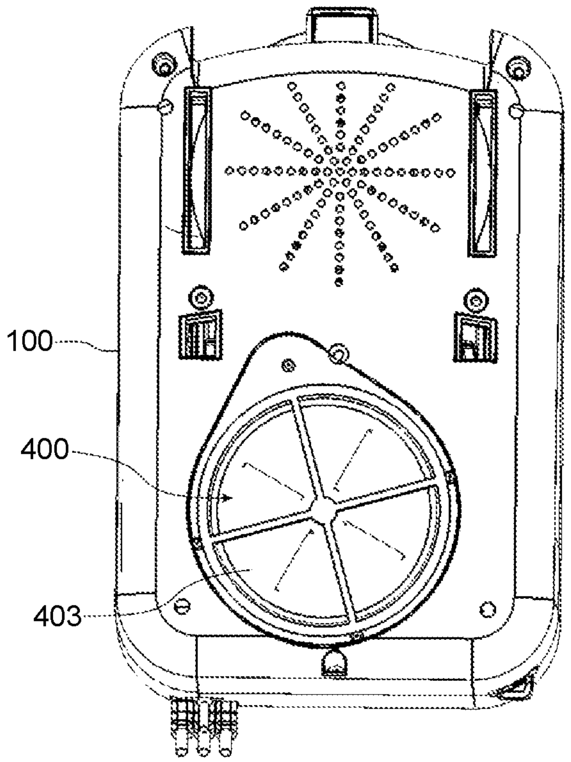
FIG. 2C is a bottom view corresponding to FIG. 2A.
Figure 3:
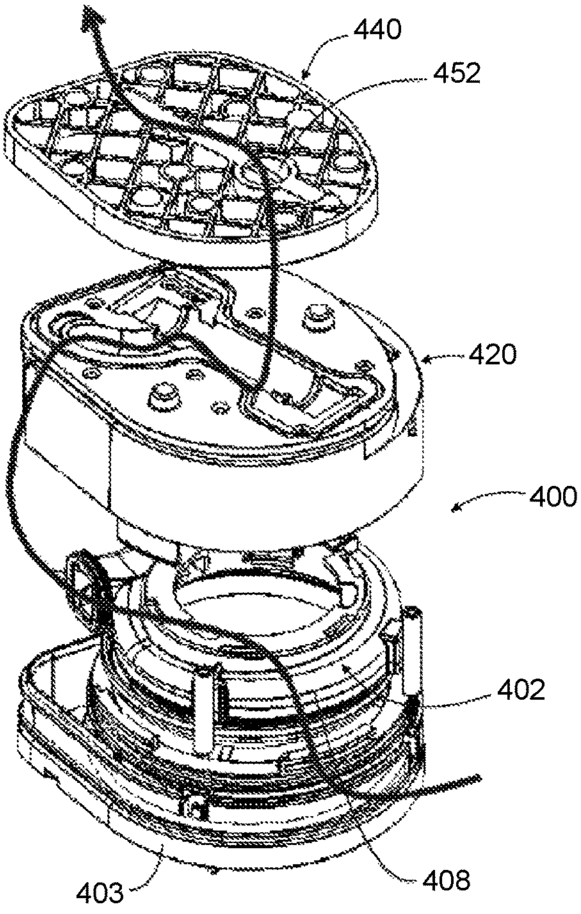
FIG. 3 is an exploded perspective view of components of a motor and/or sensor assembly schematically showing by way of an arrow the gas flow path through the assembly.

As shown in FIGS. 2 and 3 described below, the respiratory therapy apparatus 100 has various features to assist with the functioning, use, and/or configuration of the respiratory therapy apparatus 100.

Pressure is controlled by driving the flow generator 110 of the respiratory therapy apparatus 100 at the required speed to supply a desired pressure at the patient terminal end 26 of the patient interface 340, and the controller 130 is used to regulate the flow generator 110 to achieve this.

A measure of flow conductance can be used to determine if a mask is on the patient. In at least one configuration, the respiratory therapy system 1 can estimate whether or not a mask is on the patient, using a leak detection system. The leak detection system can be implemented by the controller 130. The leak detection system can comprise a maximum allowable flow threshold. The controller 130 can be configured to monitor the gas flow through the respiratory therapy system 1. The controller 130 can be operatively coupled to a flow sensor. The flow sensor can be configured to provide an indication of a measured flow rate through the respiratory therapy system 1 to the controller 130. The controller 130 is configured to compare the measured flow rate to the maximum allowable flow threshold, and provide a leak output if the measured flow rate meets a leak condition. The leak condition may be that the measured flow rate is greater than the maximum allowable flow threshold continuously during a time window. The time window may be 200 ms.

The maximum allowable flow threshold can be a constant. Alternatively, the maximum allowable flow threshold can be a function of a measured pressure and a measured pressure derivative. The maximum allowable flow threshold can additionally be a function of a vent conductance indicative of the conductance of the vent arrangement 25, a maximum leak conductance (Cmax) indicative of a hypothetical leak that emulates a maximum allowable leak at the measured flow rate, and a lung compliance indicative of the compliance of the user's respiratory system (the user's airway and/or lungs) that is in fluid communication with the respiratory therapy system 1. The maximum leak conductance may be a function of the measured flow rate and measured pressure. For example, the maximum leak conductance may be:

$$C\text{max} = \frac{F}{\sqrt{P}}$$

Upon detection of excessive leak, the respiratory therapy system 1 may provide the leak output in the form of a visual or audible alert. Excessive leak may be used as an indicator that the patient interface 340 has been disconnected from the patient. Changes to excessive leak, such as a transition from excessive leak to an acceptable leak level, may be used as an indication that the patient interface 340 has been positioned correctly on the patient's face. The leak output can be a first audible tone that sounds upon detection of, for example, meeting an excessive leak condition. A transition from a condition from where the leak condition is not met, to a leak condition that is met, may be used as an indication that the patient interface 340 has been disconnected from the patient's face. In this case, the leak output can be a second audible tone that sounds upon detection of this transition. The first audible tone can be a different frequency from the second audible tone.

In some embodiments, a first pressure level is delivered at or near the patient terminal end 26 at a first time or during a first time window. The first pressure level may be delivered at or near the patient terminal end 26 once mask fit is confirmed. The controller 130 may try and control the first pressure level using a proportional-integral-derivative (PID) control system. A second pressure level can be delivered at or near the patient terminal end 26 at a second time or during a second time window. The second pressure level may be delivered at or near the patient terminal end 26 once mask fit is confirmed, and a trigger signal is received by the respiratory therapy apparatus 100 or the respiratory therapy system 1. The controller 130 may try and continuously control the second pressure level using the PID control system. Alternatively, the controller 130 may try and control the second pressure level using a second PID control system.

In one embodiment the first pressure level is equal to desired PEEP. Preferably the first pressure is 1, 2, 3, 4, 5, 6, 7 or 8 cm $H_2O$, and useful ranges may be selected between any of these values (for example, about 1 to about 8, about 1 to about 7, about 1 to about 6, about 1 to about 5, about 2 to about 8, about 2 to about 6, about 2 to about 5, about 3 to about 8, about 3 to about 5, about 4 to about 8, about 4 to about 7, about 4 to about 5, about 5 to about 8 or about 6 to about 8 cm $H_2O$). More preferably the first pressure is about 5 cm $H_2O$.

Preferably this pressure is measured using a pressure sensor within the respiratory therapy apparatus 100. Alternatively, this pressure can be measured at or near the patient interface 340. Alternatively, the pressure can be measured in the breathing conduit assembly 200. The pressure can be subsequently stored in memory of the controller 130.

The respiratory therapy apparatus 100 can be configured to respond to a trigger signal by delivering a second pressure level.

If a trigger signal is detected by the controller 130 then the second pressure level is delivered at or near the patient terminal end 26. In at least one embodiment the second pressure level is equal to desired PIP. Preferably the second pressure is 20, 21, 22, 23, 24, 25, 26, 27, 28, 29 or 30 cm $H_2O$, and useful ranges may be selected between any of these values (for example about 20 to about 30, about 30 to about 28, about 20 to about 25, about 21 to about 30, about 21 to about 27, about 21 to about 25, about 22 to about 30, about 22 to about 29, about 22 to about 25, about 23 to about 30, about 23 to about 28, about 23 to about 26, about 24 to about 30, about 24 to about 29, about 24 to about 28, about 24 to about 26 or about 25 to about 30 cm $H_2O$).

In some embodiments 40, 42, 44, 46, 48, 50, 52, 54, 56, 58 or 60 inflations per minute are administered to the patient, and useful ranges may be selected between any of these values. The inflations can be administered with an inspiratory time of 0.30, 0.32, 0.34, 0.36, 0.38, 0.40, 0.42, 0.44, 0.46, 0.48 or 0.50 seconds, and useful ranges may be selected between any of these values.

In some embodiments a higher pressure can be administered in to the patient in the first, second, third, fourth or fifth inflations.

In at least one embodiment, the trigger signal is provided by actuation of a trigger 320.

As discussed, the controller 130 may revert to the first pressure level once a further signal is detected, or the signal ceases. Once a trigger signal is received by the controller 130, the controller 130 may change the target pressure from a first pressure level to a second pressure level, or maintain the target pressure at the second pressure level for the duration that the trigger signal continues to be received by the controller 130. Once the trigger 320 stops being actuated, or the trigger 320 signal ceases to be generated, the controller 130 may revert the target pressure to the first pressure level.

It may also be that the reverse occurs. That is, the target pressure may be set at a first pressure level for the duration that the trigger signal is received by the controller 130, and subsequently set at a second pressure level once the trigger signal is no longer received.

In one configuration, the trigger signal may be indicative of the trigger 320 being initially actuated, the trigger signal not continuing continuously for the duration that the trigger 320 remains actuated. The target pressure may initially be set at a first pressure level, and is then changed to a second pressure level when the trigger signal is received by the controller 130. The trigger signal may then only be sent again after the trigger is actuated. The controller 130 receiving the actuation signal may then causes the target pressure level to revert to the first pressure level.

In one configuration the trigger 320 may comprise at least two separate triggers that correspond to two distinct trigger signals. The controller 130 may set a target pressure at one pressure level when one trigger signal is received, and then set a target pressure at a different pressure level when the other trigger signal is received by the controller 130.

The trigger signal may be used to initiate automatic ventilation of the patient. For example, without requiring further actuation of the trigger. In such a case, once automatic ventilation begins, the respiratory therapy system may cycle between PEEP and PIP at regular time intervals based on a desired respiratory rate. The desired respiratory rate may be set by the user, or may be set as a stored setting in the controller 130.

The user and/or respiratory therapy system 1 may also monitor the patient's breathing rate, provide suction to clear fluids, and deliver surfactant to reduce the tendency of lung collapse. In at least one configuration, the surfactant can be provided to the patient in the gas flow.

In at least one embodiment, the respiratory therapy system 1 may be configured to control the flow generator 110 to compensate for an altitude that the respiratory therapy system 1 may be located. The controller 130 can be configured to use a signal provided by one or more of the sensors 30, 31 and 32, such as the flow, temperature, humidity, and/or pressure sensors to estimate an altitude, or calculate an altitude parameter of the respiratory therapy system 1. The altitude parameter may be indicative of the altitude at which the respiratory therapy system 1 is being used. The controller 130 can be configured to use the estimated altitude and/or the altitude parameter to adjust the operation of flow generator 110. This may allow a more accurate PIP and PEEP to be delivered to the patient.

PIP and PEEP pressure levels are typically determined or measured relative to ambient pressure, thus compensating for altitude and/or ambient pressure may make the PEEP/PIP control more accurate.

The respiratory therapy system 1 may compensate for ambient pressure, such that any pressure levels set is relative to ambient pressure. This may be achieved through the use of a gauge pressure sensor in a pressure control algorithm, where the gauge pressure sensor measures the difference between the pressure in the gases flow and the ambient pressure. Alternatively, the pressure signal used could be the difference in the measurement between two absolute pressure sensors, one of which is exposed to ambient air and the other which is placed in the gases flow path.

In at least one embodiment, the respiratory therapy system 1 can be configured to monitor a heart rate of the patient. In at least one embodiment, the respiratory therapy system 1 can be configured to monitor a blood oxygen concentration (for example, peripheral capillary oxygen saturation (SpO2)) of the patient. The respiratory therapy system 1 can monitor the heart rate and the blood oxygen concentration of the patient simultaneously. The heart rate and/or the blood oxygen concentration of the patient can be measured using a pulse oximeter. The respiratory therapy system 1 may be configured to communicate with the pulse oximeter to receive heart rate and/or blood oxygen concentration data. The respiratory therapy system 1 may be configured to directly, or wirelessly connect to the pulse oximeter. For example, the respiratory therapy apparatus 100 may be configured to wirelessly or directly (i.e. via a physical electronic connection, e.g. a wired connection) communicate with the pulse oximeter. The heart rate and/or the blood oxygen concentration can be displayed on the user interface 140.

2. RESPIRATORY THERAPY APPARATUS 100

An example of a respiratory therapy apparatus 100 is shown in FIGS. 2 and 3. The respiratory therapy apparatus 100 comprises a main housing having an upper chassis 102 and a main housing lower chassis 202.

The main housing upper chassis 102 has a peripheral wall arrangement 106. The peripheral wall arrangement 106 defines a humidifier or liquid chamber bay 108 for receipt of a removable liquid chamber 300. The removable liquid chamber 300 contains a suitable liquid such as water for humidifying gases that will be delivered to a patient.

In the form shown, the peripheral wall arrangement 106 of the main housing upper chassis 102 comprises a substantially vertical left side outer wall 115. The peripheral wall arrangement 106 comprises a substantially vertical left side inner wall 112. The peripheral wall arrangement 106 comprises an interconnecting wall 114. The left side outer wall 115 is oriented in a front-to-rear direction of the main housing. The left side inner wall 112 is oriented in a front-to-rear direction of the main housing. The interconnecting wall 114 extends between and interconnects upper ends of the left side inner and outer walls 115, 112. The main housing upper chassis 102 further comprises a substantially vertical right side outer wall 116. The right side outer wall 116 is oriented in a front-to-rear direction of the respiratory therapy apparatus 100. The main housing upper chassis 102 comprises a substantially vertical right side inner wall 118. The substantially vertical right side inner wall 118 is oriented in a front-to-rear direction of the main housing. The main housing upper chassis 102 comprises a second interconnecting wall 120. The second interconnecting wall 120 extends between and interconnects upper ends of the right side inner and outer walls 116, 118. The interconnecting walls 114, 120 are angled towards respective outer edges of the main housing. Alternatively, the interconnecting walls 114, 120 can be substantially horizontal or inwardly angled.

The main housing upper chassis 102 further comprises a substantially vertical rear outer wall 122. An upper part of the main housing upper chassis 102 comprises a forwardly angled surface 124. The surface 124 has a recess for receipt of a user interface 140. In one form, the user interface 140 can comprise a display. In one form, the user interface 140 can be in the form of a user interface module. A third interconnecting wall 128 extends between and interconnects the upper end of the rear outer wall 122 and the rear edge of the surface 124.

A substantially vertical wall portion extends downwardly from a front end of the surface 124. A substantially horizontal wall portion extends forwardly from a lower end of the wall portion to form a ledge. A substantially vertical wall portion extends downwardly from a front end of the wall portion and terminates at a substantially horizontal floor portion of the liquid chamber bay. The left side inner wall 112, right side inner wall 118, wall portion, and floor portion together define the liquid chamber bay. The floor portion of the liquid chamber bay has a recess to receive a heater arrangement. The heater arrangement can comprise the humidifier heating element. The heater arrangement can comprise a heater plate or other suitable heating element(s) for heating liquid in the liquid chamber 300 for use during a humidification process. The heater plate can be in thermal communication with the humidifier heating element. The humidifier heating element may therefore transfer heat to the heater plate. The heater plate can thereby transfer heat from the humidifier heating element to the liquid chamber 300. The humidifier heating element can comprise one or more resistive heating components. The humidifier heating element can comprise one or more resistive heating tracks.

The respiratory therapy apparatus 100 includes a flow generator 110 that is generally comprised of a motor 402 with an impeller that operates to deliver gases to the patient interface via the humidifier 120. The removable liquid chamber 300 comprises an outer housing 302 defining a liquid reservoir, a liquid chamber gases inlet port 306 in fluid communication with the liquid reservoir, and a liquid chamber gases outlet port 308 in fluid communication with the liquid reservoir. The respiratory therapy apparatus 100 comprises a handle/lever 500 for assisting with insertion and/or retention and/or removal of the liquid chamber 300 in and/or from the chamber bay 108. Different configurations may be configured for assisting with one, two, or all of insertion, retention, removal of the liquid chamber 300 in and/or from the chamber bay 108. The handle/lever 500 is pivotally attached to the main housing 100.

The respiratory therapy apparatus 100 shown in FIG. 2A also includes a connection manifold arrangement 351 that comprises a manifold gases outlet port 352 that is in fluid communication, via a fixed L shaped elbow, with the gas flow passage from the flow generator. The connection manifold arrangement 351 further comprises a manifold gases inlet port 350 (humidified gases return) that is embodied in a removable elbow.

Shown in FIG. 2C is the underside of the respiratory therapy apparatus 100. The respiratory therapy apparatus 100 provides a chamber shaped to receive a motor assembly 400 that is removable. The interior wall of the recess may be provided with guides and/or mounting features to assist with locating and/or attaching the motor 400 in the recess. The motor assembly 400 is a blower and comprises a motor 402 with an impeller that operates as a blower to deliver gases to the patient interface 340 via the liquid chamber 300. It will be appreciated that the shape of the chamber can vary depending on the shape of the motor assembly 400.

Figure 4:
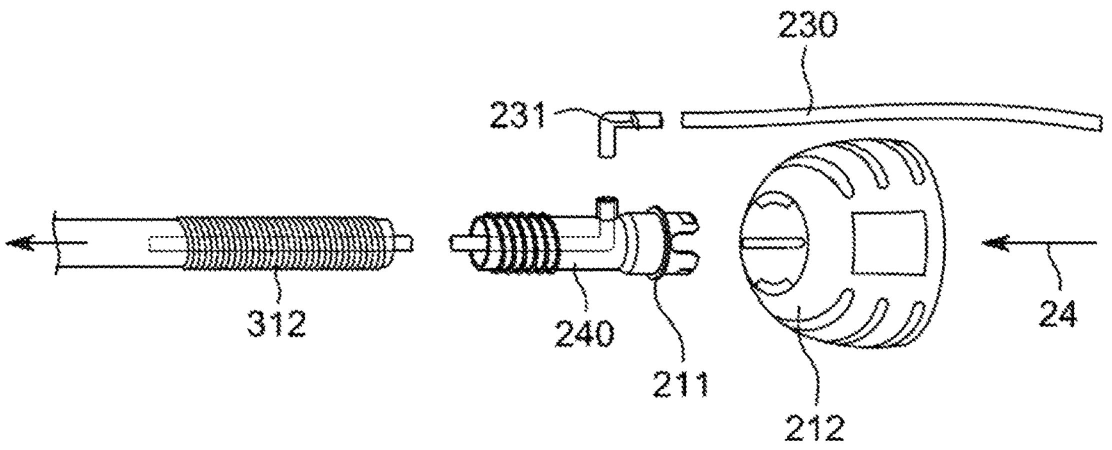
FIG. 4 is a side view of a patient end connector and sensor line passing within a breathing conduit (part thereof shown).

In the form shown in FIG. 3, the motor assembly 400 comprises a stacked arrangement of three main components; a base 403, an outlet gas flow path and sensing component layer 420 positioned above the base 403, and a cover layer 440. The sensing component layer 420 may be, or comprise, a sensing unit or a sensing module. The base 403, the sensing component layer 420, and the cover layer 440 assemble together to form a motor and/or sensor assembly 400 that has a shape that is complementary to that of the motor recess so that the motor assembly and/or sensor 400 can be received in the motor recess. The motor 402 has a body 408 that defines an impeller chamber that contains an impeller. The motor could be any suitable gas blower motor, and may for example be a motor and impeller assembly of the type described in published PCT specification WO2013/009193. FIG. 4 shows the passage of gas through the impeller and out of the motor via the gas outlet port 452 where the gas then passes to the humidifier 120.

A breathing conduit assembly 200 is coupled to a gas flow output 344 of the respiratory therapy apparatus 100, and is coupled to a patient interface 340.

3. BREATHING CONDUIT ASSEMBLY 200

The breathing conduit assembly 200 conducts air flow from the respiratory therapy apparatus 100 to the patient interface 340.

Broadly speaking the breathing conduit assembly 200 comprises a tube adapted to connect to the respiratory therapy apparatus 100, and to connect to the patient interface 340. The breathing conduit assembly 200 is configured to provide a pneumatic connection between the respiratory therapy apparatus 100 and the patient interface 340. The breathing conduit assembly 200 typically includes a heated breathing conduit 210 to reduce internal condensation, such as through the use of a heating element 220 that extends through the breathing conduit 210. An example of a heated breathing conduit is shown in PCT patent application published as WO 2012/164407A1 incorporated by reference. The patient interface 340 may removably connect to the breathing conduit assembly 200.

Various connectors for connecting the breathing conduit assembly 200 to the respiratory therapy apparatus 100 and/or the patient interface 340 are described in PCT patent application published as WO 2017/077485A1 incorporated by reference.

4. PATIENT INTERFACE 340

As discussed above, the respiratory therapy system 1 comprises a breathing conduit assembly 200 for receiving humidified gases from the respiratory therapy apparatus 100 and directing the gas flow toward the patient interface 340.

It should be appreciated reference to a patient interface 340 may comprise any one or combination of the following types: a face mask configured to at least partially, or preferably to substantially seal with the face of the patient, an oral mask configured to at least partially, or preferably to substantially seal in or around the mouth of the patient, an oronasal mask configured to at least partially, or preferably to substantially seal in or around the mouth of the patient, and in or around one or more nares of the patient or around the patient's nose, a nasal mask configured to at least partially, or preferably to substantially seal in or around one or more nares of the patient, or around the patient's nose, one or a pair of nasal prongs, an endotracheal tube, a T-piece resuscitator respiratory therapy apparatus 100, a gas flow regulator or gas pressure regulator associated with any one or more of these, although this list should not be seen as limiting. In one form, the one or a pair of nasal prongs can be configured to at least partially, or preferably to substantially seal in or around one or more nares of the patient.

A neonatal interface may be any interface, such as described above, that is configured for use with a neonate. The neonatal interface may be configured to at least partially, and preferably substantially seal around the nose and mouth of the patient.

The use of the respiratory therapy system 1 provides improved functionality for therapy, for example, in comparison to a respiratory therapy system that uses a wall source to provide the flow of gases. Thus the setup of the respiratory therapy system 1 as described provides improved functionality to resuscitation. For example, the use of a respiratory therapy apparatus 100 as described may provide for the detection of an excessive leak condition, allowing notification of the user allowing the user to mitigate the patient interface leak. Patient interface leak is the portion of the flow at the patient terminal end 26 which doesn't directly interact with the nose and/or mouth of the patient. Detection of patient interface leak helps to ensure appropriate and/or effective delivery of therapy to a patient. For example, if an excessive leak is detected in the patient interface, it may be that the patient interface 340 needs to be adjusted or replaced. The respiratory therapy system 1 may also include functionality that allows it to determine if the patient interface 340 needs to be adjusted or replaced, and then if replaced, effect automatic ordering of one or more parts, or generate a request for service. In relation to determining if the patient interface 340 needs to be adjusted or replaced, the controller 130 of the respiratory therapy apparatus 100 may generate one or more messages for the user for display on a user interface 140. The one or more messages can include tips and/or suggestions for improving patient interface fit. In at least one form, the respiratory therapy system 1 may generate an audible signal indicating that patient interface leak is within acceptable levels (e.g. a target leak flow rate range). For example, the respiratory therapy apparatus 100 may generate the audible signal. The audible signal can be a noise at a first frequency or within a first frequency range. The respiratory therapy respiratory therapy apparatus 100 may generate a leak audible signal indicating that mask leak is outside acceptable levels (e.g. a target leak flow rate range). The leak audible signal indicating that mask leak is outside acceptable levels may be a different frequency to the audible signal indicating that patient interface leak is within acceptable levels.

5. CONNECTOR ELEMENT 310

In one embodiment a connector element 310 is provided for use with the respiratory therapy system 1, the connector element 310 conveying gases to a patient requiring resuscitation and/or breathing assistance. The connector element 310 comprises a housing that comprises:

- an inlet 314 adapted to be in fluid communication or integrated with a respiratory therapy apparatus 100 that provides a supply of breathable gases,
- an outlet 316 adapted to be in fluid communication with a patient interface 340, and
- a trigger 320 that produces a signal detectable by a trigger sensor 33 on, or in, the respiratory therapy apparatus 100.

Upon detection of the trigger signal (whether directly [e.g. pneumatic or electrical signal], or indirectly [e.g. wirelessly]), the controller 130 of the respiratory therapy apparatus 100 is configured to adjust the target gas pressure provided to the inlet of the connector element 310.

Figure 9A:
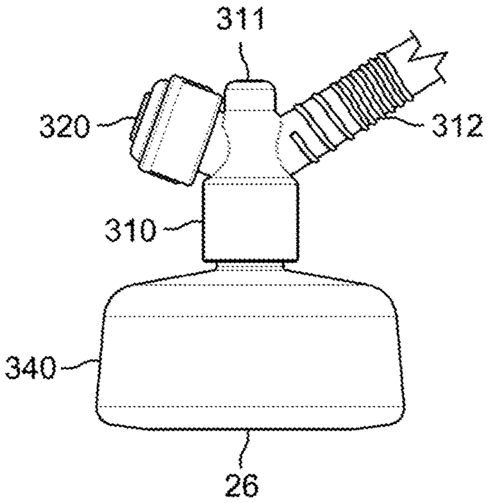
FIGS. 9A and 9*b* are side and front views of a patient interface of one embodiment as described.
Figure 9B:
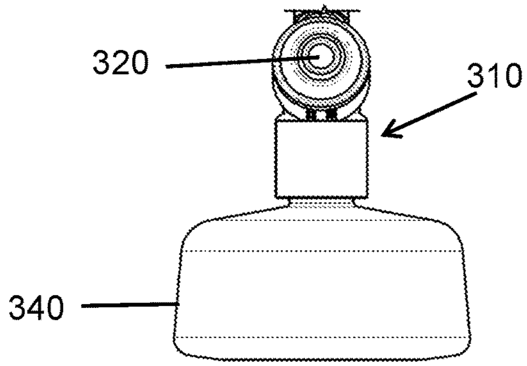

The connector element 310 may be configured to be removably connected to the breathing conduit assembly 200. The connector element 310 may be configured to be removably connected to the patient interface 340. The connector element 310 may be connected directly to the breathing conduit assembly 200, for example by being connected to the breathing conduit 210. In an illustrated configuration shown in FIG. 9A, the connector element 310 may be configured to be connected to an interface conduit 312. The interface conduit 312 defines an intermediate conduit between the connector element 310 and the breathing conduit 210. The interface conduit 312 may be configured to be removably connected to the breathing conduit 210.

The interface conduit 312 may have a different diameter to that of the breathing conduit 210. The external diameter and/or cross-sectional area of the interface conduit 312 may be less than the internal diameter of the breathing conduit 210. The external diameter of the interface conduit 312 may be less than the external diameter of the breathing conduit 210. The internal diameter of the interface conduit 312 may be less than the internal diameter of the breathing conduit 210. In one embodiment the breathing conduit assembly 200 comprises a patient end connector 212. The patient end connector 212 may be at the interface of the interface conduit 312 and the breathing conduit 210 to join the interface conduit 312 and the breathing conduit 210 to ensure a continuous gas flow path.

The connector element 310 may further comprise a vent arrangement 25. The vent arrangement 25 may comprise one or more holes. The vent arrangement 25 provides an opening from inside the connector element 310 to atmosphere. The vent arrangement 25 may therefore be configured to enable venting of gases from inside the connector element 310 to atmosphere. The vent arrangement 25 may assist in heat flushing from the breathing circuit (e.g. flushing excess heat that may be generated by the flow generator), reducing $CO_2$ rebreathing by the patient, and maintaining a stable oxygen concentration in the breathing conduit assembly 200.

In those configurations where the vent arrangement 25 has multiple holes, the holes may be the same size. Alternately, the holes may be of a range of sizes. In some configurations the vent arrangement 25 comprises one or more circular holes. In some configurations the vent arrangement 25 comprises one or more ellipse-shaped holes. The vent arrangement 25 may be located on one or more sites of the connector element 310. For example, the vent arrangement may be located on opposite sides of the connector element 310, and/or on the surface of the connector element 310 about the inlet 314 or outlet 316. The vent arrangement 25 may be located towards the connector element outlet 316. Alternately, the vent arrangement 25 is located proximate to the trigger 320.

The connector element 310 may comprise a monitoring port 317. The monitoring port 317 allows access to the internal space of the connector element 310, for example to allow sampling of gases in the connector element 310, or to allow introduction of compositions into the connector element 310, such as medication (e.g. surfactant).

Figure 10:
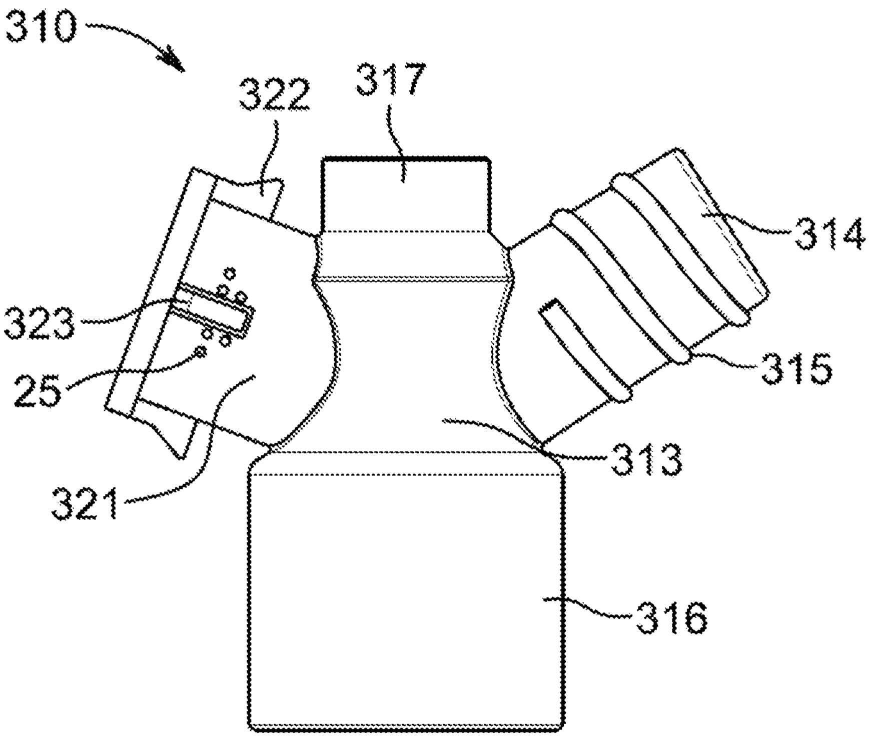
FIG. 10 is a side view of a connector element of one embodiment as described.

A specific embodiment of a connector element is shown in FIG. 10. The connector element 310 comprises a hollow cylindrical body 313 with a gases inlet 314, a gases outlet 316, and a trigger port 321. The gases inlet 314 is fluidly connected to the gases outlet 316. Also shown in FIG. 10 is a monitoring port 317. A helical rib 315 is located on the exterior of the gases inlet 314 to enable attachment of the interface conduit 312. Other forms of attachment, e.g. interference fit, push fit, snap fit or magnetic connection, are possible. The monitoring port 317 is shaped to receive a valve, such as a duck billed valve 311 as described in PCT publication WO 03/066146 incorporated by reference.

A concentric annular rim at the gases outlet 316 allows for attachment of a patient interface 340. Other shapes are envisaged for the rim of the gases outlet 316 so long as the gases outlet 316 is attachable to the patient interface 340. The interface conduit 312 can be removably connected to the gas inlet 314. The interface conduit 312 can be removably connected to the connector element 310 via an interference fit, push fit, snap fit, screw fit or magnetic connection, for example. Alternatively, the interface conduit 312 can be permanently connected to the gases inlet 314.

Figure 5:
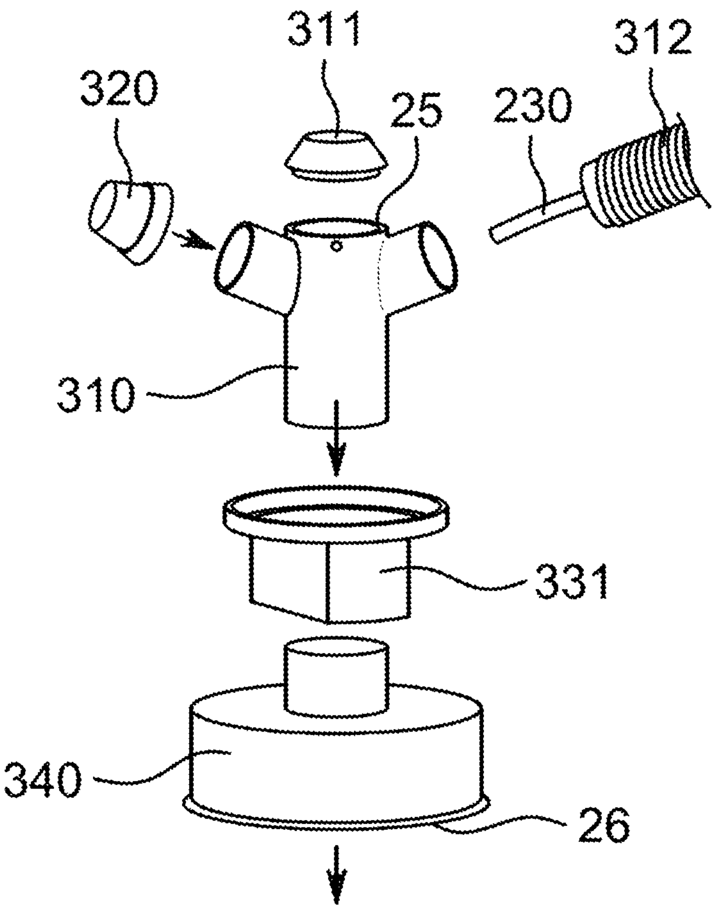
FIG. 5 is an exploded view of an embodiment showing a connector element, protective cap and patient interface.

As shown in FIG. 5, the connector element 310 may include a protective cap 331. The protective cap 331 is removed prior to the connector element 310 and patient interface 340 being coupled.

As shown in FIG. 10 the vent arrangement 5 is located on the trigger port 321. It will be appreciated that the vent arrangement 25 can be located on another portion of the connector element 310 provided they allow exhausting of gases. For example, the vent arrangement 25 can be located on the gases inlet 314 and/or the gases outlet 316. In one embodiment the vent arrangement 25 may be located on the hollow cylindrical body 313. In at least one configuration, the vent arrangement 25 can be located on the monitoring port 317. In at least one configuration, the connector element 310 may comprise more than one vent arrangement 25. For example, one or more of the gases inlet 314, gases outlet 316, monitoring port 317 and the trigger port 321 can comprise a respective vent arrangement 25.

The connector element 310 comprises one or more protrusions 322, 323. In at least one configuration, the trigger port 321 comprises the one or more protrusions 322, 323. In the configuration illustrated in FIG. 10, the connector element 310 comprises four protrusions 322, 323. The protrusions may facilitate connection of the trigger 320 to the connector element 310. In some embodiments the vent arrangement 25 is protected from occlusion by the hand of a user by being located underneath the trigger 320 with respect to the exterior of the patient interface. In other words, the vent arrangement 25 can be shielded by the trigger 320. In at least one configuration, the vent arrangement 25 is shielded by a wall of the trigger 320. A space is provided between the wall and the vent arrangement, so that the vent arrangement 25 remains fluidly connected to atmosphere.

FIGS. 18B and 18C show alternative locations for the vent arrangement 25. Within these embodiments, ribs or other projected features 319 hinder the ability of the user to accidentally occlude the vent arrangement 25.

In one embodiment the connector element 310 is "t", "T", or "Y"-shaped. Preferably the trigger port 321 and the gases inlet 314 define the arms of the "t", "T" or "Y". Preferably the gases outlet 316 defines the stem of the "t", "T" or "Y". In some embodiments the stem of the connector element 310 comprises waist region, or a zone of reduced diameter, the waist or zone being where the trigger port 321 and the gases inlet 314 join to the gases outlet 316. Preferably the arm and stem regions of the "t", "T", or "Y"-shaped connector element 310 are circular in cross-section.

As an alternate description, the connector element 310 may be formed as a cylindrical body having two or more zones of varying diameter. Preferably the diameter of the zone proximal the gases outlet 316 is greater than zones distal from the gases outlet 316. Preferably the trigger port 321 and the gases inlet 314 are cylindrical and connect to the cylindrical body of the connector element 310 at a zone of reduced diameter that defines a central portion of the connector element 310.

In those embodiments including a monitoring port 317, the monitoring port 317 may be present as an extension of the cylindrical body of the connector element 310. For example, the monitoring port 317 may extend from the central portion of the connector element 310. Preferably the monitoring port 317 may extend from the central portion of the connector element 310 as a circular projection. Preferably the projection defining the monitoring port 317 has a diameter less than that of the gases outlet 316, gases inlet 314 and trigger port 321. In one embodiment the monitoring port 317 comprises a ledge that extends the circumference of the circular projection of the monitoring port 317.

Figure 19A:
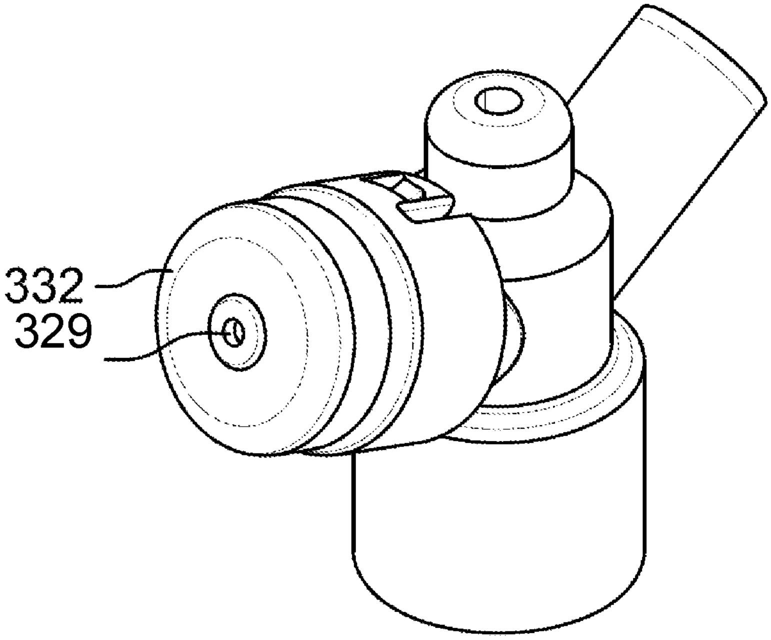
FIG. 19A is a perspective view of a connector element and trigger of one embodiment as described.
Figure 19B:
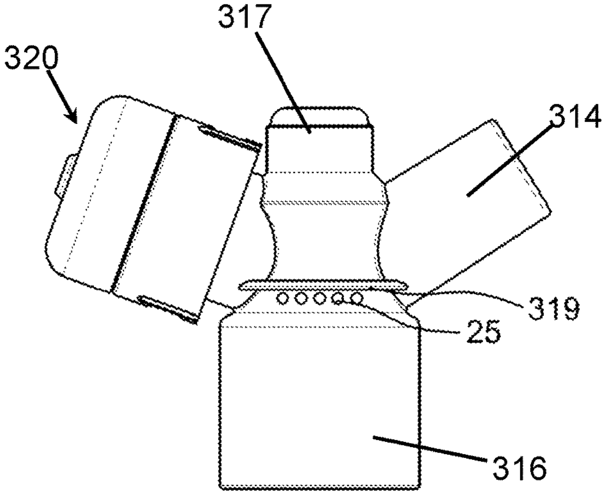
FIGS. 19B and 19C are side and perspective views of a connector element with a vent arrangement.

In some embodiments the venting arrangement 25 is located on the waist region of the connector element 310, as show in FIG. 19B. That is, the venting arrangement 25 is located on the cylindrical body of the connector element 310 where the diameter of the cylindrical body is reduced. For example, the venting arrangement 25 may be located at a central portion of the connector element 310 where the gases inlet 314 and trigger port 321 join to the cylindrical body of the connector element 310. The venting arrangement 25 may be present as one or more holes about the waist region of the cylindrical body of the connector element 310. In one embodiment the venting arrangement 25 is arranged as a concentric ring of spaced holes.

Figure 19C:
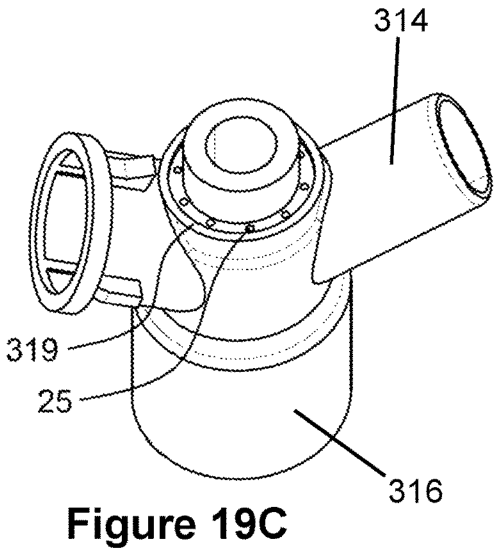

In some embodiments the venting arrangement 25 is located on the ledge that extends the circumference of the circular projection of the monitoring port 317 as shown in FIG. 19C. That is, the venting arrangement 25 is located at the base of the monitoring port where it connects to the central region of the connector element 310. The venting arrangement 25 may be present as one or more holes in the ledge. In one embodiment the venting arrangement 25 is arranged as a concentric ring of spaced holes in the ledge.

In one embodiment the connector element 310 comprises ribs or other projected features 319 adjacent or proximate the venting arrangement 25. For example, the projected features 319 may be placed above, below, or both above and below the venting arrangement 25. As shown in FIG. 19B there is a projected feature 319 located above the venting arrangement 25. The projected feature 319 may extend concentrically around the cylindrical body of the connector element 310 optionally as a continuous projection as shown in FIG. 19B, or as a series of discontinuous projections.

As shown in FIG. 19C, the projected feature 319 may extend adjacent or proximate the venting arrangement 25 located on the ledge of the monitoring port 317. The projected feature 319 may extend concentrically as a continuous projection as shown in FIG. 19C, or as a series of discontinuous projections.

6. TRIGGER ASSEMBLY AND SENSOR

As stated above, the respiratory therapy system 1 comprises a trigger 320. The trigger 320 is configured produce a signal that is detected by a trigger sensor 33 in communication with the controller 130. Once the controller 130 determines that a signal has been detected by the trigger sensor, the controller 130 is configured to control the flow generator 110 to deliver at least the first pressure or the second pressure based on use of the trigger 320.

In one embodiment the trigger 320 connects to a trigger sensor line 230, the trigger sensor line 230 providing a signal to the trigger sensor 33.

In one embodiment activation of the trigger provides a pneumatic signal to the trigger sensor 33 via the trigger sensor line 230. The trigger sensor line 230 may be detachably connectable to the trigger sensor 33.

The trigger sensor line 230 may include reinforcing ribs on at least a portion thereof of the internal lumen of the trigger sensor line 230. A benefit of the reinforcing ribs is that this may inhibit full or partial occlusion of the trigger sensor line 230 in the event that a compressive force is applied to it.

Figure 11:
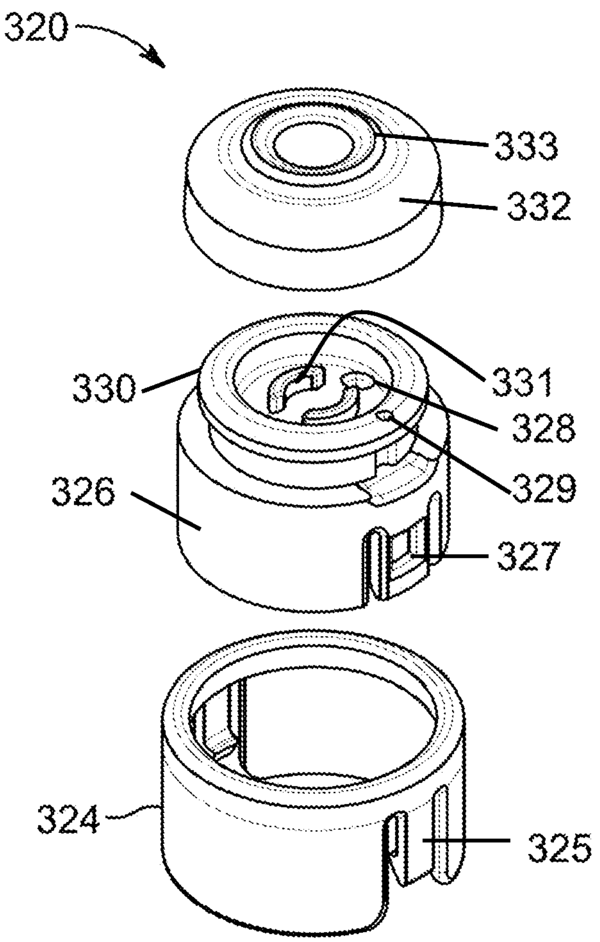
FIG. 11 is an exploded view of a trigger of one embodiment as described.
Figure 12A:
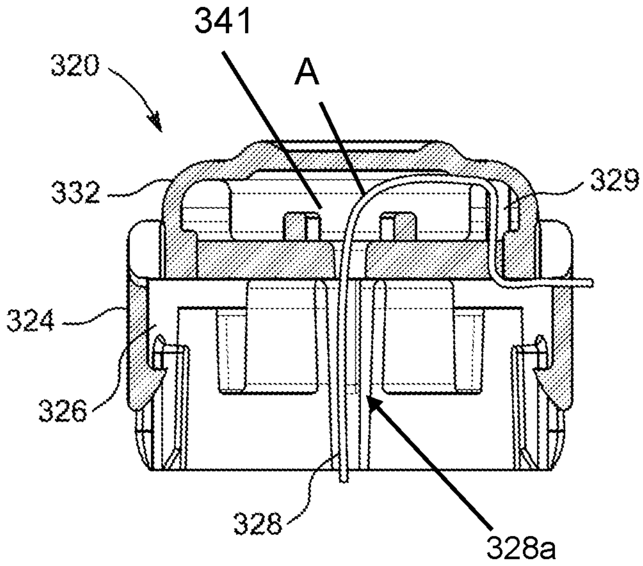
FIGS. 12A and 12B are cross-sectional views through the trigger embodiment as shown in FIG. 11.
Figure 12B:
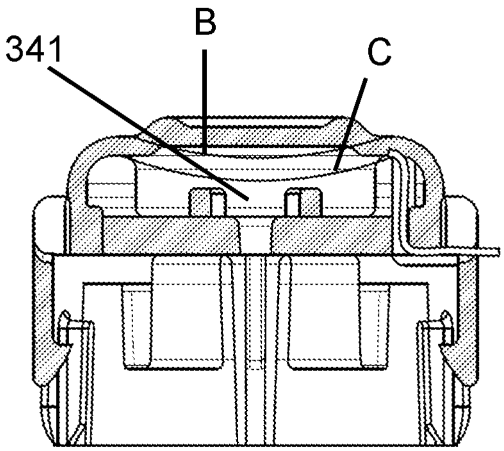
Figure 13:
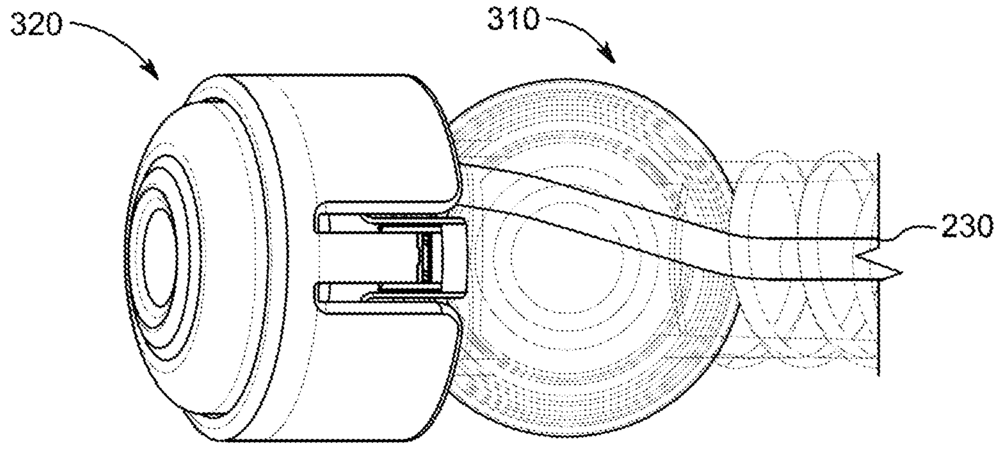
FIG. 13 shows a sensor line connector of one embodiment as described.
Figure 14:
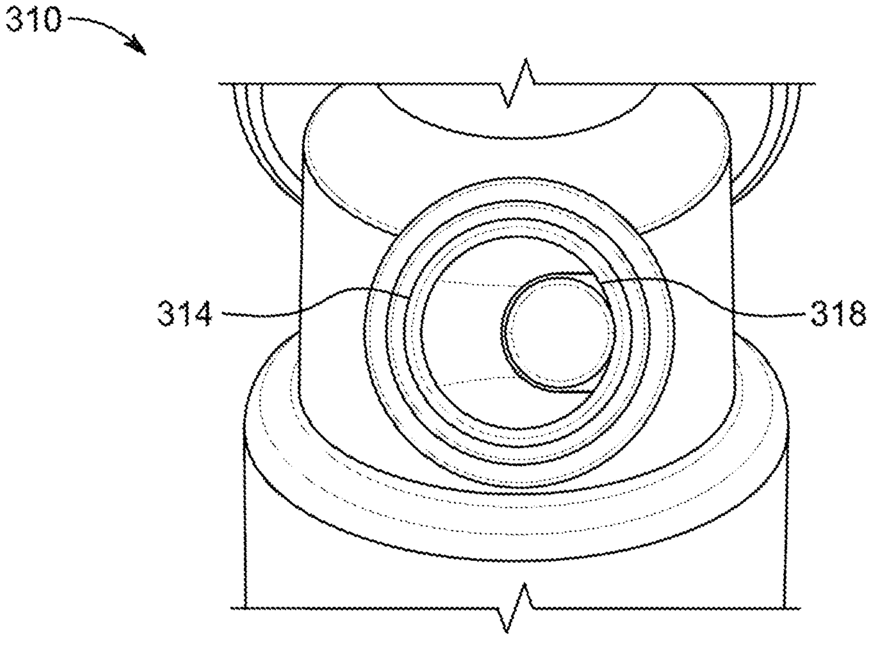
FIG. 14 shows a trigger sensor line retention mechanism of one embodiment as described.

One embodiment of a pneumatic trigger 320 is shown in FIGS. 11 to 13.

The illustrated trigger 320 comprises a housing 326 and a moveable member 332 that together define a compressible chamber 341. In the embodiment depicted in FIG. 11, the moveable member 332 is an elastomeric button. The compressible chamber 341 also includes a first trigger opening 328 and a second trigger opening 329. The trigger sensor line 230 connects to the compressible chamber 341 via the first trigger opening 328. The second trigger opening 329 provides an opening in the compressible chamber 341 to ambient conditions. The gas path through the first trigger opening 328 and the second trigger opening 329 is as indicated by gas flow "A" in FIG. 12A. The second trigger opening 329 inhibits the ability of false triggers, through variance in temperature or pressure, by use of the reference to ambient conditions.

When the moveable member 332 is depressed to point "B" (as shown in FIG. 12B) the moveable member 332 occludes the second trigger opening 329. Continued movement of the moveable member 332 to point "C" leads to increased pressure within the compressible chamber 341 generating a pneumatic trigger signal which is detected by the trigger sensor via the trigger sensor line 230 connected to the first trigger opening 328. In other words, the controller 130 is configured to monitor the pressure within the compressible chamber 341 and the trigger sensor line 230 using the trigger sensor 33. A trigger pressure within the compressible chamber 341 and the sensor line 230 can exceed a trigger pressure threshold to indicate activation of the trigger 320. The controller 130 may be configured to monitor the trigger pressure, and provide an output when the trigger pressure exceeds the trigger pressure threshold.

In some embodiments the trigger 320 comprises an attachment device 327 on the housing 326 that retains the trigger 320 on the trigger port 321. As shown in FIG. 11, the attachment device 327 comprises one or more clips that mate with corresponding retention elements on the trigger port 321.

In some embodiments the trigger 320 comprises an outer housing 324 that sits about the housing 326. Preferably the outer housing 324 comprises a housing retention member 325 that connects the housing 326 and outer housing 324 together.

In some embodiments the moveable member 332 comprises a feedback projection 333. The feedback projection may be on an upper surface of the moveable member 332. The feedback projection 333 provides haptic feedback to the user regarding the location of their thumb/finger with respect to the upper surface of the moveable member 332. It should be appreciated that the feedback projection 333 could be of any geometry that might be indicative of locating a central point, e.g. a cross, squircle or hemisphere. The presence of a feedback projection 333 may also enhance stability in the location of the thumb/finger by functionally providing a gripping surface.

In some embodiments the trigger 320 comprises a projecting collar 330 on the housing 326. Preferably the projecting collar 330 retains the moveable member 332 onto the housing. In other words, the moveable member 332 can connect to the projecting collar 330. The moveable member 332 may be removably connected to the projecting collar 330. The moveable member 332 may be permanently connected to the projecting collar 330.

A surface of the feedback projection 333 can be textured to provide a gripping surface. The trigger sensor line 230 connects to the compressible chamber 341 through the first trigger opening 328. In particular, the first trigger opening 328 may be at least partially defined by a first trigger opening collar 328*a*. The trigger sensor line 230 can connect to the first trigger port opening collar 328*a*. The trigger sensor line 230 can connect to the first trigger port opening collar 328*a* removably or permanently, with an interference fit, snap fit or the like.

In those embodiments in which the signal is a pneumatic signal, the trigger sensor 33 may be a pressure sensor that detects a change in pressure. Alternately, the trigger 320 can be a pneumatic pressure switch that converts the air pressure to an electrical signal that is then detected by a sensor in communication with the controller 130. Activation of the trigger 320 is detected by a differential pressure sensor, by way of the sensor line, which creates the trigger signal. As an alternative, the differential pressure sensor could be placed at the patient interface 340 or anywhere along the breathing conduit assembly 200 between the respiratory therapy apparatus 100 and the patient interface 340.

If the differential pressure sensor is not placed within the respiratory therapy system 1, a signal can be generated by the differential pressure sensor and sent to the respiratory therapy system 1, thus the signal could be transmitted wirelessly or by any another applicable means.

The trigger 320 may be located on the respiratory therapy apparatus 100, the breathing conduit 200, the connector element 310, or the patient interface 340. In an alternate embodiment the trigger 320 is located remote to the respiratory therapy apparatus 100, the breathing conduit assembly 200, the connector element 310, or the patient interface 340. For example, the trigger may be electrically coupled to the respiratory therapy apparatus 100 directly (i.e. wired in) or indirectly (i.e. removable plug). Alternately the trigger 320 may transmit to the flow respiratory therapy apparatus 100 such as through the use of wireless signals, such as Wi-Fi, Bluetooth, optical or infrared.

The trigger 320 may be configured produce a signal that is detected by a trigger sensor 33, and wherein the signal is an electrical signal. As shown in FIGS. 15A to 15D the trigger 320 may be a switch that, upon activation, completes a circuit which is then detected by the trigger sensor 33 or the controller 130. In reference to FIGS. 15A to 15D, the connector element 310 may include a trigger 320 in the form of, for example, a switch, located on a housing 326. The housing 326 may then locate on an outer housing 324 that locates on the connector element 310. The housing 326 and the outer housing 324 may be formed as a single unitary component. If formed as separate components, a concentric annular ring 330 may be used to attach the housing 326 to the outer housing 324. The concentric annular ring 330 may include an attachment mechanism 335 that mates with a corresponding mechanism of the outer housing 324. The attachment mechanism 335 may be in the form of an interference fit, push fit, snap fit or magnetic connection. The housing 326 may be held in position by being sandwiched between the concentric annular ring 330 and the outer housing 324. The outer housing 324 may include a helical rib that allows the housing 326, having a corresponding helical rib, to be screw attached to the outer housing 324.

Figure 15A:
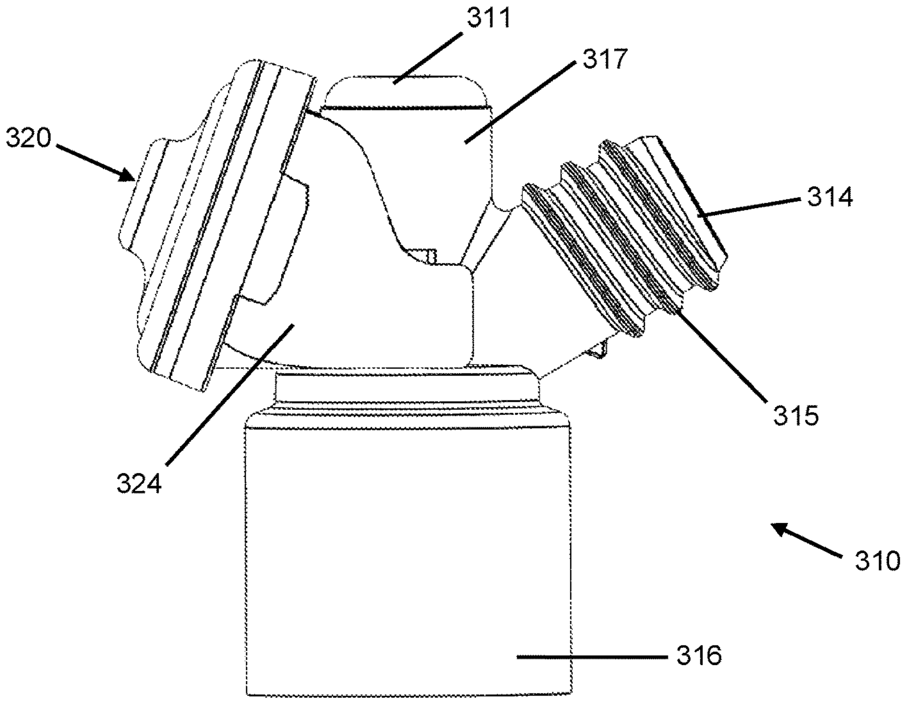
FIGS. 15A to 15D show a connector element having an electrically based trigger.
Figure 15B:
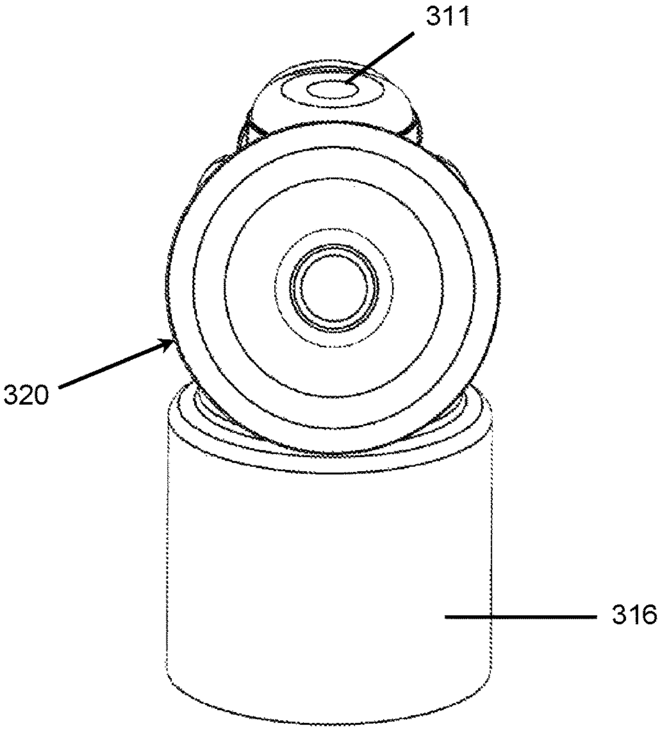
Figure 15C:
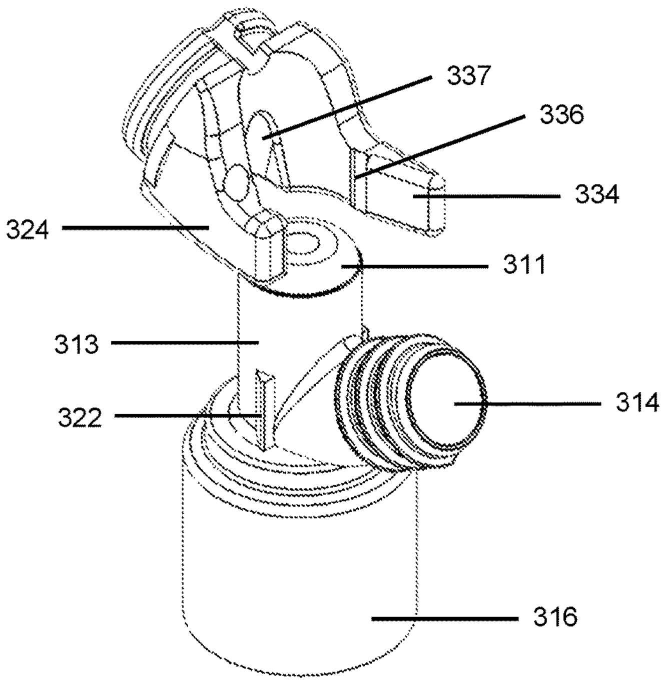
Figure 15D:
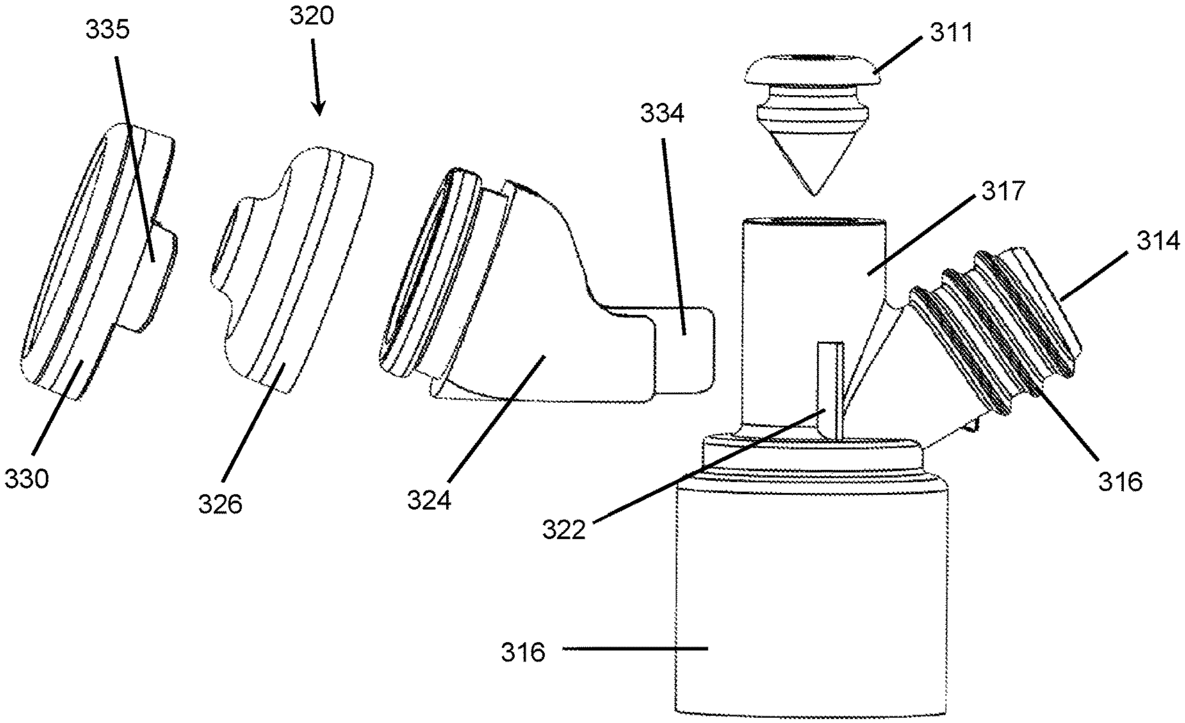
Figure 16:
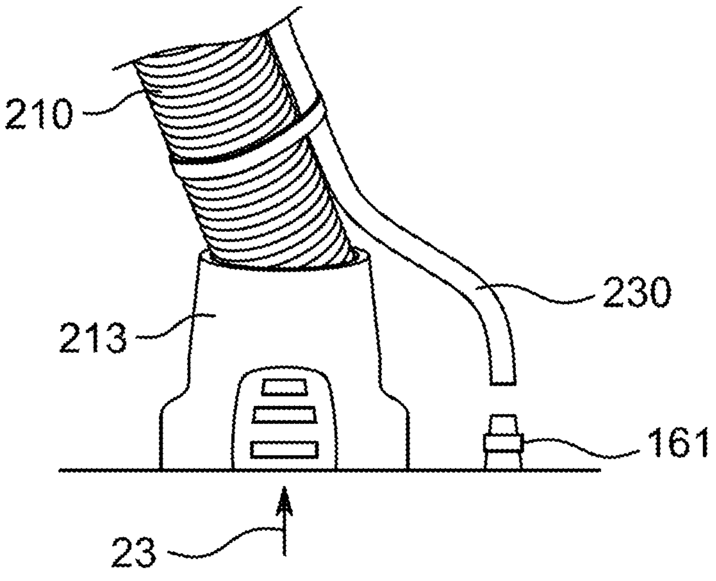
FIG. 16 is a side view of a unit end connector of one embodiment as described.

As mentioned above, the connector element may include a vent arrangement 25, to allow exhausting of gases, located on the hollow cylindrical body 313. As shown in FIG. 15C, the outer housing 324 may include a recess 337 that accommodates the vent arrangement 25 allowing the gases to exhaust via the recess 337.

The outer housing 324 may include a retention mechanism 334 that provides for its attachment (as a component of the trigger 320) to the connector element 310, for example, via a corresponding attachment mechanism 322 on the connector element 310. This may allow the trigger 320 to be removably connected to the connector element 310. As shown in FIG. 15C the outer housing 324 may include a retention mechanism 334 in the form of a clip or tab that mates to one or more protrusions 322 on the connector element 310. For example, the clip or tab of the retention mechanism 334 may be resiliently deformable to allow for attachment and detachment of the retention mechanism 334 from the one or more protrusions 322 on the connector element 310. The clip or tab may include an attachment face 336 that locates about the one or more protrusions 322 to retain the outer housing 324 to the connector element 310. In one embodiment, pressure applied to the clip or tab distal to the latching face 336 may flex the body of the outer housing 324 in a zone about the latching face 336. Flexing of the body of the outer housing 324 in this zone may at least partially disengage the retention mechanism 334 from the one or more projections 322 allowing the trigger 320 to be removed from the connector element 310. The removal of the trigger 320 may be in a vertical direction relative to the connector element 310. That is, in a direction parallel to the rotational axis of the hollow cylindrical body 313. It will be appreciated that a range of retention mechanisms could be used such as an interference fit, push fit, snap fit or magnetic connection. It will also be appreciated that the retention mechanism 334 prevents inadvertent disconnection or displacement of the trigger 320 from the connector element 310.

The trigger 320 may be located on the connector element 310. When located on the connector element 310, preferably the trigger 320 is located on the trigger port 321. The trigger 320 may be detachable from the trigger port 321.

Having the trigger 320 and its components (i.e. housing 326 and/or outer housing 324 if present) removably connectable may allow the trigger 320 to be reprocessed after used and therefore subsequently reused.

A removably connectable trigger 320 may also allow the trigger 320 to be actuated from a position remote from the connector element 310. For example, in a use condition a first person may hold the patient interface 340 in place over the patient's mouth and/or nose (as is appropriate), with a second person then controlling actuation of the trigger 320. The trigger 320 may include an extendable sensor line that, for example, may remain coiled within, or on, the connector element 310 when in the retracted position.

As mentioned above, the trigger sensor 33 may detect an electrical signal that is generated when the trigger 320 is actuated. The electrical signal may generate solely when the trigger 320 is actuated, which each subsequent actuation of the trigger 320 providing an electrical signal for the trigger sensor 33. For example, actuation of the trigger 320 may generate an electrical signal that is detected by the trigger sensor 33 that causes the controller 130 of the respiratory therapy apparatus 100 to adjust the target gas pressure provided to the inlet of the connector element 310 to a first pressure level. Subsequent actuation of the trigger 320 may generate an electrical signal that is detected by the trigger sensor 33 that causes the controller 130 of the respiratory therapy apparatus 100 to adjust the target gas pressure provided to the inlet of the connector element 310 to a second pressure level.

Alternately, actuation of the trigger 320 may generate an electrical signal that is detected by the trigger sensor 33 that causes the controller 130 of the respiratory therapy apparatus 100 to adjust the target gas pressure provided to the inlet of the connector element 310 to a first pressure level for the duration that the trigger 320 is actuated. That is, once the trigger 320 is no longer actuated the controller 130 adjusts the target gas pressure provided to the inlet of the connector element 310 to a second pressure level.

The electrical switch may have two or more positions, wherein an electrical signal is delivered when the switch is in one of the positions. The switch may be biased to a default position, such that movement out of the default position generates an electrical signal causing the controller 130 to adjust the target gas pressure to a first pressure level. Release of the switch may return the switch to the default position causing the controller 130 to adjust the target gas pressure to a second pressure level. The switch may not be biased, instead requiring the user to move the switch between the two or more positions.

The trigger 320 may comprise two or more electrical switches, wherein an electrical signal is generated when a user actuates the first switch, the electrical signal generation only ceasing when the user actuates a second or subsequent switch. That is, the electrical signal causes the controller 130 to adjust the target gas pressure to a first pressure level, and adjusts to a second pressure level when the signal generation ceases.

When using an electrical switch, this may have a benefit that the controller 130 can automatically determine when the trigger has been correctly connected. For example, the controller 130 may detect the resistance in the circuit to determine if there is a correct connection, by comparing the detected resistance against a stored reference.

A portion of the trigger sensor line 230 may pass through at least a portion of the interface conduit 312, terminating inside the connector element 310 at the trigger 320. Including a portion of the trigger sensor line 230 within the interface conduit 312 enhances usability of the patient interface by minimising obstructions for the user. An alternative embodiment could comprise the trigger sensor line 230 being disposed externally on the patient interface 340. This may assist in reducing resistance to flow for the main gas path. In an alternate embodiment the interface conduit 312 may be a multi-lumen line and wherein the sensor line passes between the lumen layers.

In one embodiment, the trigger 320 is pneumatic, with the trigger 320 taking the form of a compressible chamber 341.

FIGS. 18A to 18C show an alternative connector element 310 to that described above. The connector element 310 of FIGS. 18A to 18C provide an alternative pathway for the ambient reference by inclusion of an atmospheric reference orifice 329 in the moveable member 332. In this embodiment the housing 326 and a moveable member 332 together define a compressible chamber 341. As shown for FIG. 11, the moveable member 332 may comprise a feedback projection 333 on its upper surface. The feedback projection 333 provides haptic feedback to the user regarding the location of their thumb/finger with respect to the upper surface of the moveable member 332. It should be appreciated that the feedback projection 333 could be of any geometry that might be indicative of locating a central point, e.g. a cross, squircle or hemisphere. The presence of a feedback projection 333 may also enhance stability in the location of the thumb/finger by functionally providing a gripping surface. Thus, when the user places their thumb or finger on the moveable member 332 to generate a signal, the finger or thumb also occludes the atmospheric reference orifice 329.

In some embodiments the trigger sensor line 230 may extend on the outside of the breathing conduit assembly 200, or a portion thereof, when the trigger 320 is located on the breathing conduit assembly 200 or connector element 310 or patient interface 340. In such embodiments the breathing conduit assembly 200 may comprise a retention element) that retains the trigger sensor line 230. The retention element may be a clip or a sleeve that holds the trigger sensor line 230 to the breathing conduit assembly 200.

As shown in FIG. 4, in a preferred embodiment the trigger sensor line 230 extends from the first trigger opening 328 (or first trigger port opening collar 328*a*) through the interface conduit 312, out through a side wall of the interface conduit 312 to an elbow 231, and along the length of the breathing conduit 210 to a sensor port 161.

In some embodiments the trigger sensor line 230 may extend on the inside of the breathing conduit 210, or a portion thereof, when the trigger 320 is located on the breathing conduit 210, connector element 310 or patient interface 340.

Preferably the trigger sensor line 230 does not obstruct access of any peripheral equipment to the connector element 310. This is particularly shown in FIG. 13 in which the orientation of the trigger 320 results in orientation of orifice 328 in a manner which means the trigger sensor line 230 does not obstruct access of any peripheral equipment through the duck billed valve and/or the monitoring port.

Figure 7A:
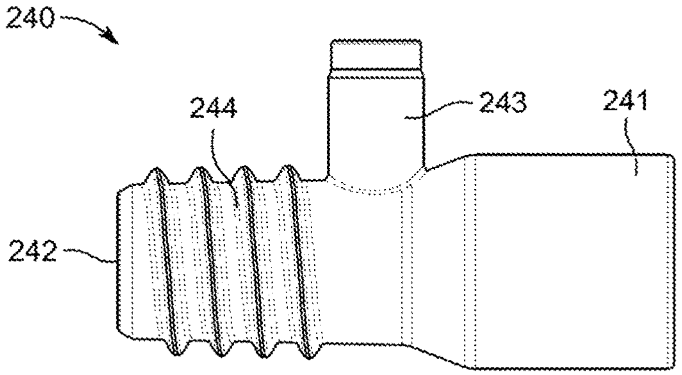
FIGS. 7A and 7B are a side view and a front view of a sensor line connector of one embodiment as described.
Figure 7B:
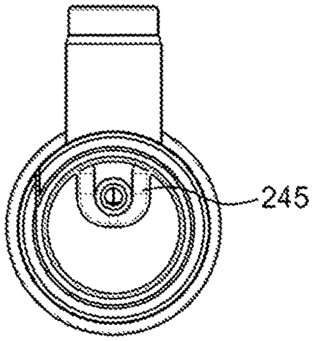
Figure 8:
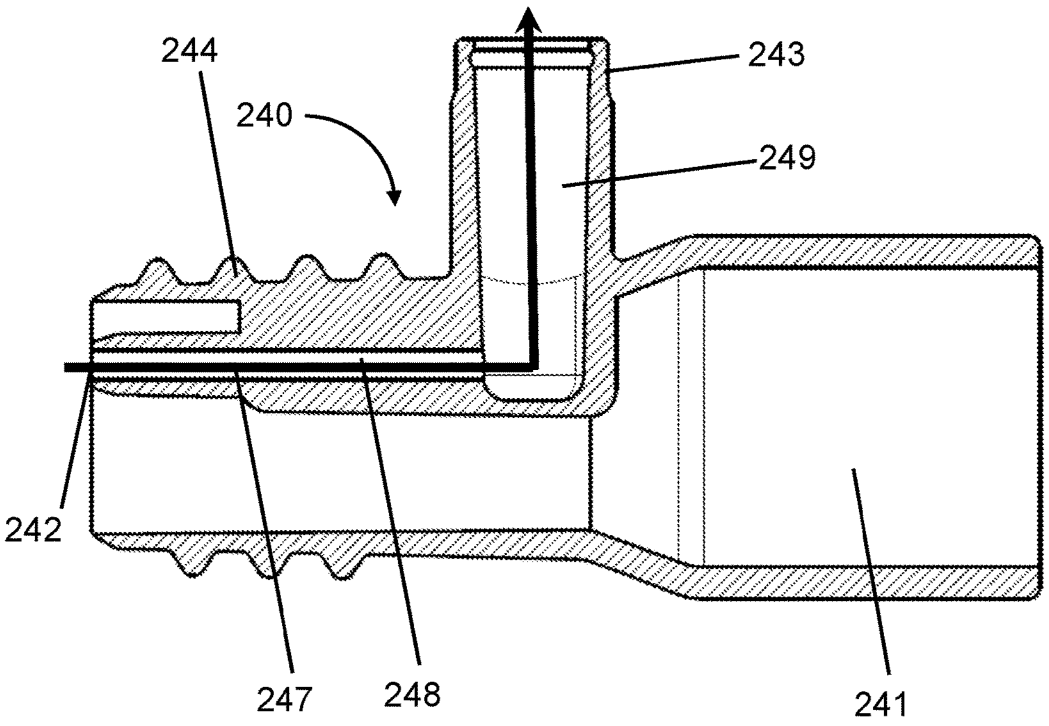
FIG. 8 is a cross-sectional view of the sensor line connector of FIGS. 7A and 7B.

In one embodiment the respiratory therapy system 1 comprises a sensor line connector 240. An example of a sensor line connector 240 is shown in FIGS. 7A and 7B. As seen in FIGS. 7A and 7B, the sensor line connector 240 includes a cylindrical hollow body with a sensor line connector gases inlet 241 and sensor line connector gases outlet 242, further comprising a line connection port 243. The internal diameter of the gases inlet is substantially similar to the external diameter of the gases outlet of the interface connector 211 which allows for coaxial connection. The external diameter of the gases outlet 242 comprises a helical rib 244 with a pitch substantially similar to an optional bead of the interface tube 312 which can allow for coaxial connection by winding the interface tube onto the sensor line connector 240. The trigger sensor line 230 can comprise a first sensor line portion and a second sensor line portion. The first sensor line portion can be configured to connect to the first trigger opening 238. The second sensor line portion can be configured to connect to sensor port 161. A sensor line port 245 within the lumen of the sensor line connector from the line connection port 243 provides the pneumatic pathway between a first sensor line portion and second sensor line portion. The sensor line port 245 is shaped to minimise the flow resistance imposed on the main gases path 24. A cross-section of the sensor line connector, as shown in FIG. 8, highlights the pneumatic pathway 247 for the trigger sensor line 230.

Figure 6:
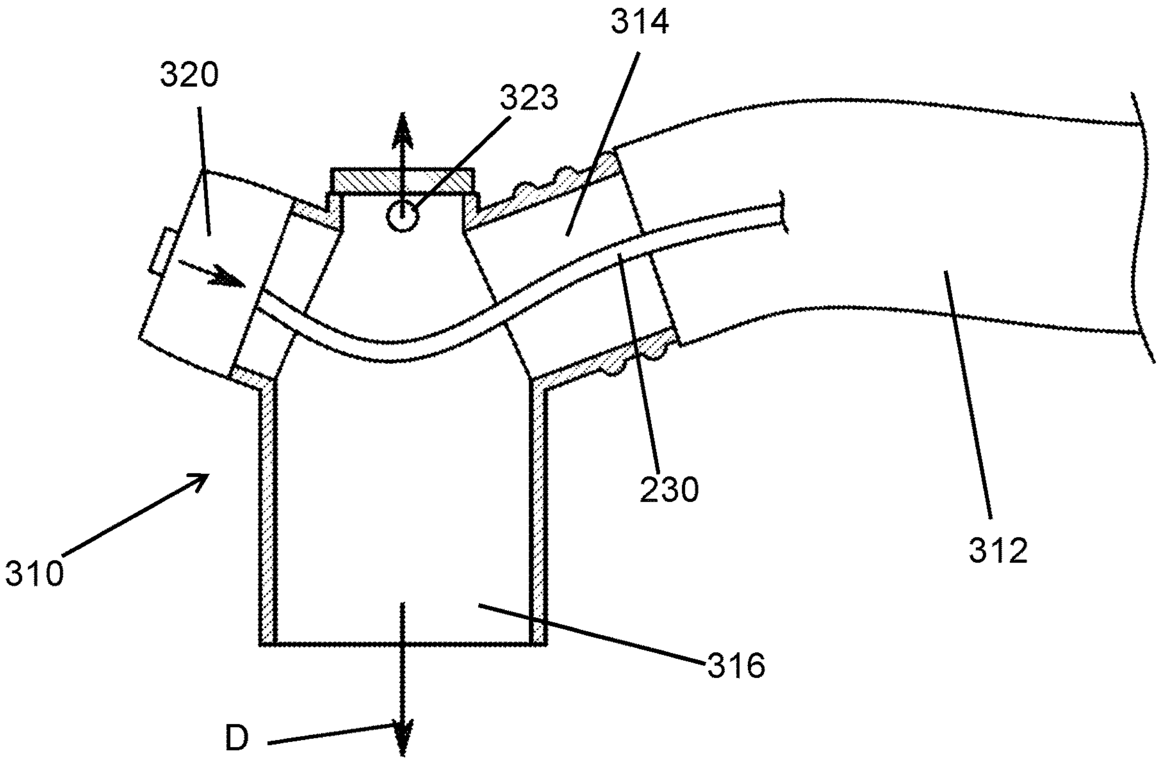
FIG. 6 is a cross-sectional view of the patient end connector, and the sensor line passing within the interface or breathing conduit (part thereof shown).

In at least one embodiment as shown in FIG. 4, there is provided a sensor line connector 240 for connection between a patient interface 340 and an interface conduit 312. As shown by the arrow "D" in FIG. 6, the main pathway of the breathable gas path is via a patient end connector 212 and through the internal portion of the breathing conduit assembly 200. Other patient end connectors 212 are described in WO 2017/037660A1, which is incorporated by reference. In this embodiment the trigger sensor line 230 passes externally to an elbow connector 231 to a sensor line connection located inside the breathing conduit 210.

Thus, the first sensor line portion 248 is at least partially disposed within the interface conduit 312. In some embodiments this may further be substantially coaxial.

As mentioned above, in an alternative embodiment the trigger sensor line 230 may be external to the interface conduit 312. For a connection between the interface conduit 312 and the breathing conduit 210, an interface connector 211 and patient end connector 212 is utilised. In one embodiment as shown, the interface connector 211 and the patient end connector 212 are separate elements. In an alternate embodiment, the interface connector 211 and the patient end connector 212 may be formed as a unitary interface connector and patient end connector. In addition, the interface connector 211 and the patient end connector 212 may also incorporate the sensor line connector 240.

The patient end connector 212 is the point at which the breathing conduit assembly 200, and the heating wire 220, terminates. The breathing conduit assembly 200 may further comprise a conduit sensor 32. The conduit sensor 32 may be configured to provide an indication of the temperature of gases near the patient end connector 212. The controller 130 is configured to monitor the conduit sensor 32. The interface conduit 312 and the breathing conduit 210 may have dissimilar diameters. Alternatively, the interface conduit 312 and the breathing conduit 210 may have dissimilar cross-sectional profiles. The interface connector 211 predominantly allows for connection between dissimilar cross-sectional profiles of the interface conduit 312 and the breathing conduit 210. The cross-sectional profile of the interface conduit 312 may be smaller than the cross-sectional profile of the breathing conduit 210. In other words, the cross-sectional area of the interface conduit 312 may be smaller than the cross-sectional area of the breathing conduit 210. In at least one configuration, the diameter of the interface conduit 312 may be smaller than the diameter of the breathing conduit 210.

Other interface connectors are described in WO 2013/022356A1, which is incorporated by reference.

Figure 17:
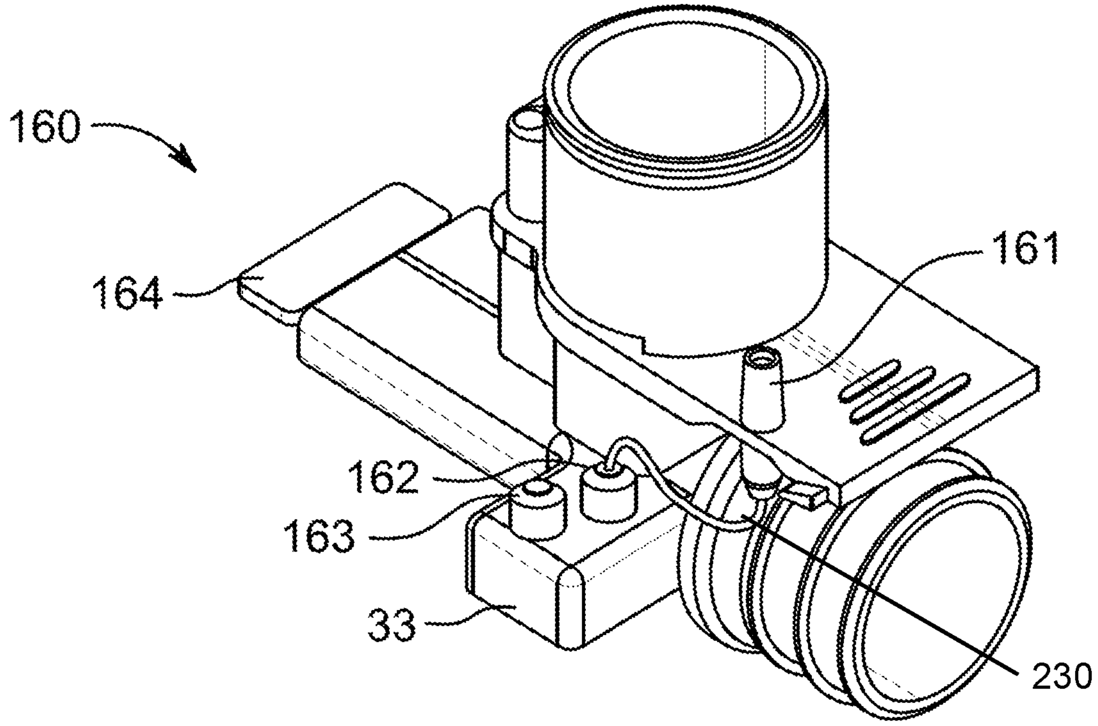
FIG. 17 is a perspective view of a gas outlet of one embodiment as described.

In one embodiment the respiratory therapy apparatus 100 comprises a removable gases outlet 160. As shown in FIG. 17 the removable gases outlet 160 comprises the sensor port 161. The device sensor 33 is operably coupled to the sensor port 161. The device sensor 33 can therefore provide an indication of a measurable parameter at the sensor port 161. The device sensor 33 is operatively coupled to the controller 13. The controller 13 may therefore receive an indication of a measurable parameter using the device sensor 33. The device sensor 33 of this embodiment is a differential pressure sensor. The device sensor 33 comprises a first port 162 to measure the pressure within the compressible chamber. The device sensor 33 comprises a second port 163 to define an ambient pressure reference. The removable gases outlet 160 includes a trigger sensor line 230 between the sensor port 161 and the first port 162. This device sensor 33 is connected to the controller 130 through an electrical connection 164. The trigger sensor line 230 can be operatively coupled to the device sensor 33. For example, the trigger sensor line 230 can connect to the sensor port 161.

Figure 20:
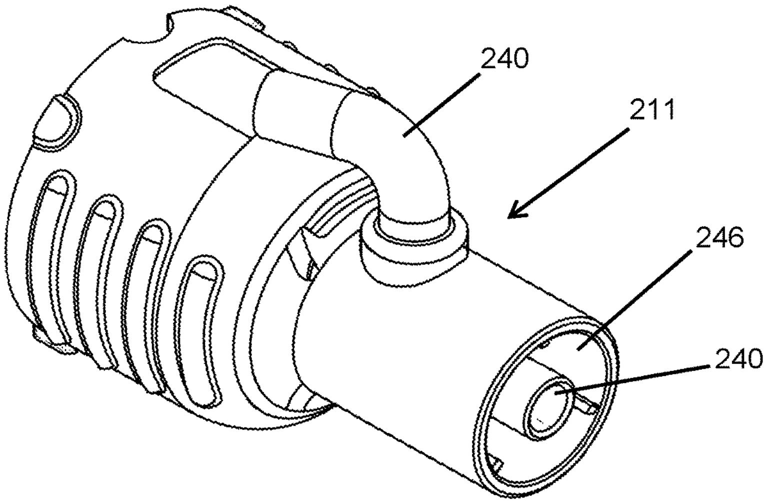
FIG. 20 is a perspective view of an interface connector of one embodiment as described.
Figure 21:
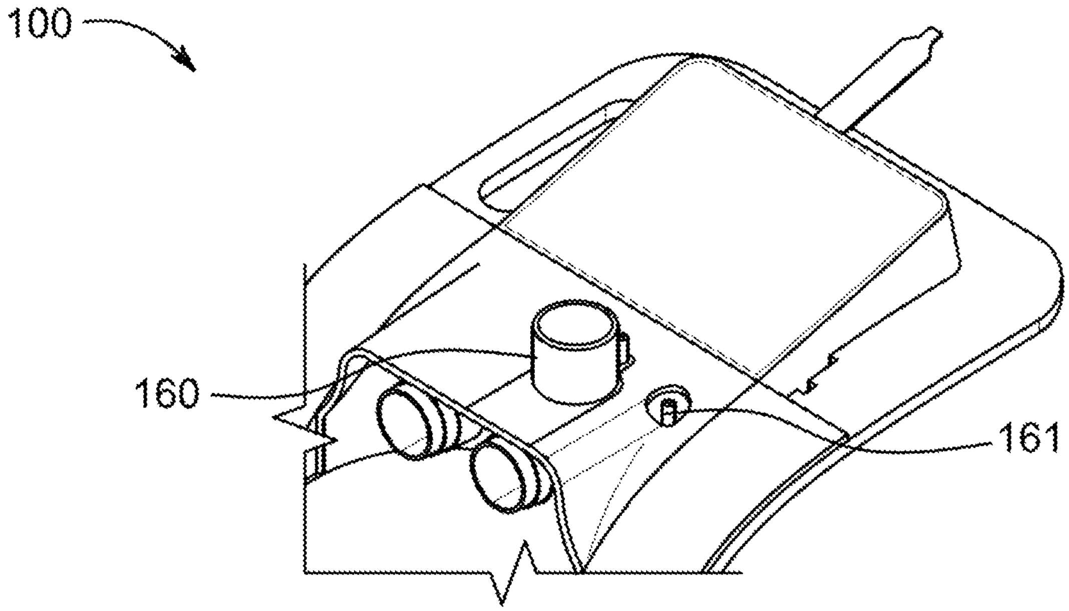
FIG. 21 is a perspective view of a sensor port housing of one embodiment as described.

As shown in FIG. 20 is an alternative interface connector 211 which further comprises the features of the sensor line connector 240. The alternative interface connector 211 comprises an elbow 240 that transitions the trigger sensor line 230 from external to the alternative interface connector 211 to internal to the alternative interface connector 211. In one embodiment the alternative interface connector 211 comprises an internal conduit 246. Preferably the sensor line passes within the internal conduit 246. The internal diameter of the interface connector 211 is substantially similar to the external diameter of the interface conduit 312 which allows for coaxial connection.

In one embodiment the trigger may be a biased trigger. That is, the moveable member 332 may be moveable between a first position and a second position, and biased towards the first position.

Thus, the trigger 320 is moveable between an inactivated state and an active state. Preferably the active state is when the trigger 320 generates a signal or detection by the trigger sensor 33. Preferably when the trigger 320 in an active position the respiratory therapy apparatus 100 adjusts gas pressure provided from a first pressure to a second pressure. More preferably when the trigger 320 is in the active position the gas pressure is adjusted from PEEP to PIP. The active position may correspond to the active state of the trigger 320. A non-active position may correspond to a non-active state of the trigger 320. The moveable member 332 may be moveable between the active position and the non-active position. The inactive position may correspond with the first position. The active position may correspond with the second position.

In one embodiment activation of the trigger 320 initiates a sequence of automated breaths at 30, 35, 40, 45, 50, 55, 60 breaths/min, and useful ranges may be selected between any of these values (for example, about 30 to about 60, about 30 to about 50, about 30 to about 45, about 35 to about 60, about 35 to about 45, about 40 to about 60, about 45 to about 60 breaths/min).

In one embodiment the activation of the trigger provides the sequence of automatic breaths until the trigger is activated again. In one embodiment the activation of the trigger provides the sequence of automatic breaths until the patient interface is removed. In one embodiment the activation of the trigger provides the sequence of automatic breaths for the duration that the trigger is continuously activated.

7. USER INTERFACE

The user interface is configured to provide a visual output to the patient and/or user. The user interface 140 can be configured to provide a visual output representing a state or therapy parameter of the respiratory therapy system 1. The user interface is configured to deliver the messages to the patient and/or user. The user interface may include a wireless communication system or a remote computer such as a tablet.

Figure 18:
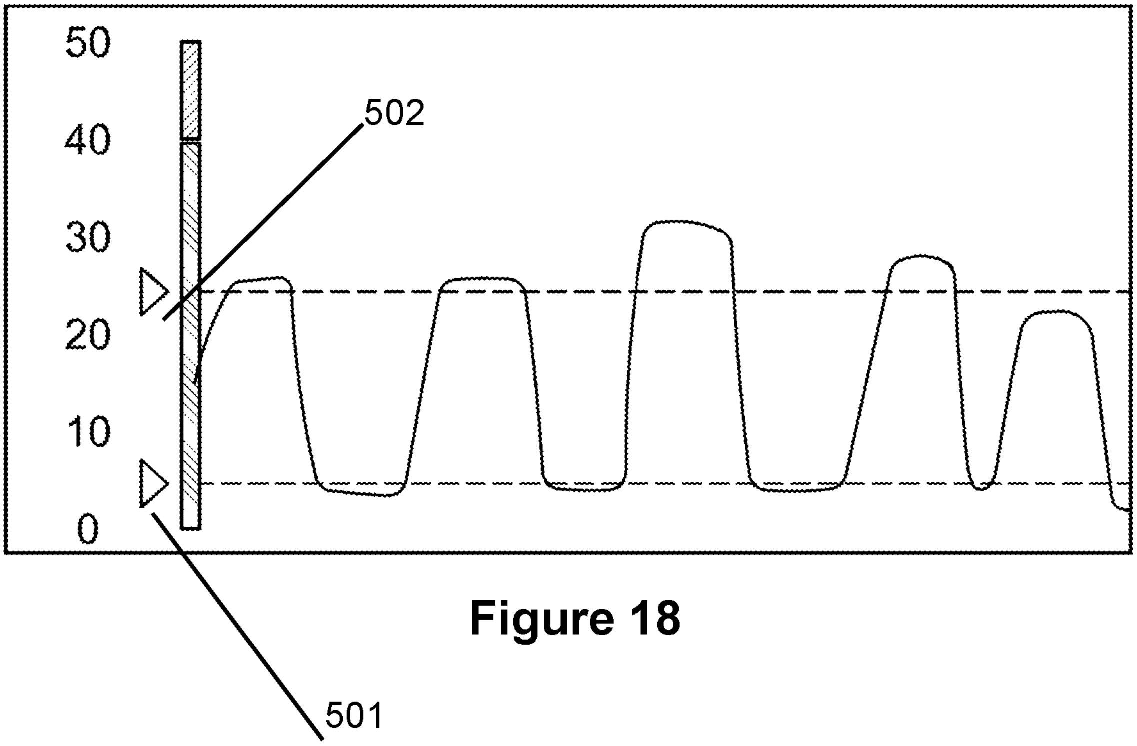
FIG. 18 shows an output indicative of the output displayed on a user interface when the respiratory therapy apparatus as described is utilised.

In some embodiments the user interface 140 may comprise a touch screen display that provides information to a patient or user of the respiratory therapy system 1. In some embodiments the information may be about the status of the respiratory therapy system 1 or a component thereof, status of the therapy being provided, status of a patient, and/or status of an accessory or peripheral associated with the respiratory therapy system 1. The display may comprise one or more indicia that each provide information about a respective aspect of the therapy; for example gas temperature, oxygen concentration, gas flow rate, blood oxygen concentration (SpO2), and heart rate. Other indicia may also be provided. The indicia may also act as touch screen 'buttons' where pushing on one of the indicia enables a user to change a setting of an aspect of the therapy, of the respiratory therapy system 1, and/or of an accessory or peripheral associated with the respiratory therapy system 1, which then causes the controller 130 to adjust the respiratory therapy system 1 or accessory or peripheral to that new setting As shown in FIG. 18 is an example of a user interface 140 that comprises a touchscreen used to oversee and control operation of the device 100. Suitable user interfaces are described in WO 2019/112447A1 incorporated by reference which provides disclosure of a graphical user interface controlling a respiratory therapy apparatus 100.

Within the proposed system, the touchscreen can provide a graphical real-time display of pressure delivered to the patient at the terminal end 26 during use, an example of which is shown within FIG. 18. The solid waveform providing an indication of the delivered pressure with dotted lines indicative of the desired PIP 502 and PEEP 501. The touchscreen may further include start/stop button to initiate or halt therapy, target PIP setting to define the delivered PIP, target PEEP setting to define the delivered PEEP, and an indication of breath rate delivered based on the rate at which the user triggers PIP delivery.

The invention claimed is:

1. A respiratory therapy system, the respiratory therapy system comprising:

- a respiratory therapy apparatus, configured to provide a flow of breathable gas at, at least a first pressure and a second pressure to a patient, the respiratory therapy apparatus comprising;
  - a flow generator configured to provide the flow of breathable gas,
  - a controller, coupled to a trigger sensor, to control respiratory therapy apparatus operations;
- a breathing conduit assembly that conveys the breathable gas to a patient via a patient interface;
- a removably connectable trigger, configured to be actuated from a position remote from the patient interface, that produces a signal detectable by the trigger sensor;
- a connector element disposed between the breathing conduit assembly and the patient interface;
- a removably connectable trigger that is removably attached to the connector element, the trigger configured to be actuated from a position sufficiently remote from the connector element to allow a first person to hold the patient interface in place over a patient's mouth and/or nose, and a second person to control actuation of the trigger, that produces a signal detectable by the trigger sensor;
- wherein the trigger comprises a pneumatic compressible chamber integrated with the breathing conduit assembly;
- wherein the controller is configured to:
  - maintain positive end expiratory pressure (PEEP) as a baseline therapy pressure;
  - detect a compressible-chamber pressure exceeding a predefined threshold indicative of user actuation; and
  - in response, temporarily deliver peak inspiratory pressure (PIP) for a duration of trigger actuation, automatically reverting to PEEP upon release of the trigger; and
- wherein the trigger does not modify stored therapy parameters.

2. The respiratory therapy system of claim 1, wherein the trigger is connected to the trigger sensor via a trigger sensor line.

3. The respiratory therapy system of claim 1, wherein the trigger sensor is configured to provide an output to the controller indicative of a compressible chamber pressure.

4. The respiratory therapy system of claim 1, wherein the trigger sensor is a gauge, absolute or differential pressure sensor.

5. The respiratory therapy system of claim 3, wherein the controller is configured to control the respiratory therapy system to deliver the first pressure when the compressible chamber pressure is below a compressible chamber pressure threshold, and the second pressure when the compressible chamber pressure is above the compressible chamber pressure threshold.

6. The respiratory therapy system of claim 3, wherein the controller is configured to control the respiratory therapy system to deliver the second pressure when the compressible chamber pressure is below a compressible chamber pressure threshold, and the first pressure when the compressible chamber pressure is above the compressible chamber pressure threshold.

7. The respiratory therapy system of claim 2, wherein the trigger sensor line is located externally of the breathing conduit assembly.

8. The respiratory therapy system of claim 2, wherein the trigger sensor line is located internally of the breathing conduit assembly.

9. The respiratory therapy system of claim 1, wherein the connector has a first outlet in fluid communication with the patient interface, an inlet in fluid communication with the breathing conduit assembly, and an opening that defines a chamber.

10. The respiratory therapy system of claim 2, wherein a portion of the trigger sensor line terminates inside a connector at the trigger.

11. The respiratory therapy system of claim 1 wherein the respiratory therapy apparatus comprises a vent arrangement.

12. The respiratory therapy system of claim 1, wherein the trigger is a pneumatic trigger comprising a housing and a moveable member, wherein the housing and the moveable member at least partially define the compressible chamber.

13. The respiratory therapy system of claim 12, wherein the trigger comprises a plurality of projections within the compressible chamber to define a boundary for an inward deflection of the moveable member.

* * * * *